US009606108B2

United States Patent
Krishnan et al.

(10) Patent No.: US 9,606,108 B2
(45) Date of Patent: Mar. 28, 2017

(54) DEFORMABLE PLATFORMS FOR BIOLOGICAL ASSAYS

(71) Applicant: President and Fellows of Harvard College, Cambridge, MA (US)

(72) Inventors: Ramaswamy Krishnan, Cambridge, MA (US); Allen Ehrlicher, Boston, MA (US); James Butler, Brookline, MA (US); David A. Weitz, Bolton, MA (US); Jeffrey J. Fredberg, Sharon, MA (US); Chan Young Park, Belmont, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/358,891

(22) PCT Filed: Nov. 16, 2012

(86) PCT No.: PCT/US2012/065597
§ 371 (c)(1),
(2) Date: May 16, 2014

(87) PCT Pub. No.: WO2013/074972
PCT Pub. Date: May 23, 2013

(65) Prior Publication Data
US 2014/0336072 A1   Nov. 13, 2014

Related U.S. Application Data

(60) Provisional application No. 61/560,448, filed on Nov. 16, 2011.

(51) Int. Cl.
G01N 33/50   (2006.01)
C12M 1/00   (2006.01)
(Continued)

(52) U.S. Cl.
CPC ......... *G01N 33/5029* (2013.01); *B05D 3/007* (2013.01); *B32B 37/24* (2013.01);
(Continued)

(58) Field of Classification Search
None
See application file for complete search history.

(56) References Cited

U.S. PATENT DOCUMENTS

2006/0240548 A1*  10/2006  Deutsch ............... B01L 3/5027
                                                435/305.2
2009/0015928 A1    1/2009   Crosby et al.
(Continued)

FOREIGN PATENT DOCUMENTS

WO    WO 2010/011407    *  1/2010

OTHER PUBLICATIONS

Gilchrist et al., "Measurement of intracellular strain on deformable substrates with texture correlation." Journal of Biomechanics, 40(4):786-794 (2007).
(Continued)

*Primary Examiner* — Betty Forman
(74) *Attorney, Agent, or Firm* — Mintz Levin Cohn Ferris Glovsky and Popeo, P.C.

(57) ABSTRACT

A platform for biological assays includes a base substrate providing structural support to the platform, at least one surface of the base substrate coated with position markers, a first deformable layer positioned on top of the base substrate, and a second deformable layer positioned on top of the first deformable layer, the second deformable layer embedded with deformation markers.

15 Claims, 19 Drawing Sheets

(51) Int. Cl.
*C12M 1/12* (2006.01)
*B05D 3/00* (2006.01)
*B32B 37/24* (2006.01)
*G01N 33/483* (2006.01)

(52) U.S. Cl.
CPC ............ *C12M 23/20* (2013.01); *C12M 25/14* (2013.01); *G01N 33/4833* (2013.01); *B32B 2037/243* (2013.01); *G01N 2500/10* (2013.01); *Y10T 156/10* (2015.01)

(56) References Cited

U.S. PATENT DOCUMENTS

| | | |
|---|---|---|
| 2009/0298191 A1 | 12/2009 | Whitesides et al. |
| 2010/0330644 A1 | 12/2010 | Feinberg et al. |
| 2011/0104798 A1 | 5/2011 | Tschumperlin et al. |
| 2011/0117603 A1 | 5/2011 | Piparia et al. |
| 2011/0189719 A1 | 8/2011 | Kuo et al. |

OTHER PUBLICATIONS

James H-C Wang et al., "Cell traction force and measurement methods." Biomechanics and Modeling in Mechanobiology, 6(6):361-371 (2007).

\* cited by examiner

DEFORMABLE PLATFORMS FOR BIOLOGICAL ASSAYS

RELATED APPLICATIONS

This application is a national stage application, filed under 35 U.S.C. §371, of International Application No. PCT/US2012/065597 filed on Nov. 16, 2012, which claims the priority to U.S. provisional application U.S. Ser. No. 61/560,448 filed Nov. 16, 2011, the contents which are hereby incorporated by reference in their entirety.

STATEMENT AS TO FEDERALLY SPONSORED RESEARCH

This invention was made with U.S. government support under grant number 5R01HL065960 from the National Institutes of Health, and grant numbers NSF DMR-1006546 and DMR-0820484. The government has certain rights in the invention.

FIELD OF INVENTION

The present disclosure relates generally to platforms for biological assays and more particularly to deformable platforms for biological assays in cell traction force microscopy.

BACKGROUND

The physical environment of a living cell and mechanical stress exerted at cell-substrate and cell-cell interfaces affects a number of physiological processes. Reproducing and measuring such stresses and the effect on cells, e.g., measuring traction forces exerted by cells on a substrate, has been a challenge.

SUMMARY OF INVENTION

The invention provides compositions, systems, and methods for culturing cells on substrates with the stiffness/softness profiles of physiological tissues and for measuring forces exerted by the cells on their substrate in the presence and absence of test agents in screens to identify therapeutic compounds.

A change in the softness or stiffness of the surfaces on which or in which the cells reside leads to changes in their function, behavior, gene expression and other parameters. Cells respond to mechanical stimulation by changes in physiological processes such as growth, differentiation, tumorigenesis, or metastatic potential. The invention provides compositions such as defined mechanical media for cell culture and methods by with to measure or track behavioral changes of the cells in response to the mechanical media.

In one aspect, the disclosure provides a platform for biological assays, the platform including a base substrate providing structural support to the platform, at least one surface of the base substrate coated with position markers, a first deformable layer positioned on top of the base substrate, and a second deformable layer positioned on top of the first deformable layer, the second deformable layer embedded with deformation markers.

Implementations of the platform may provide one or more of the following features. Polymer gels are used to make the deformable substrates. Preferred substrates are fabricated from silicone polymers such as polydimethylsiloxane (PDMS). Exemplary polymer compositions include Silgard™ and NuSil™. Preferably, the deformable layers do not comprise a hydrogel composition. The first and second deformable layers are made of a primarily same material; and the first and second deformation layers are combined and merged into an indistinguishable layer with deformation markers embedded near an outer surface of the indistinguishable layer. The stiffness of at least one of the first and second deformable layers is tunable. At least one of the first and second deformable layers is primarily made of a silicone polymer such as PDMS. At least one of the first and second deformable layers has a stiffness (Young's modulus) less than 10 kilopascal (kPa).

The position markers and the deformation markers comprise a detectable composition, e.g., a fluorescent compound, an index-mismatch compound, or a light scattering compound. For example, the deformation markers are fluorescent beads, alternatively non-fluorescent beads or other particles visualized by techniques such as phase contrast or absolute/differential interference contrast microscopy, or scattering objects such as gold nano-particles. These alternatives can describe the wide variety of ways in which the position data may be read out. The position markers and the deformation markers have different fluorescent colors. A layer of color A beads lies directly on the supporting stiff surface of the device, upon which is coated the first deformable layer with a thickness of about 50-300 μm, on top of which is the second deformable layer with a thickness of about 1-5 μm which includes a layer of color B beads. The color B deformation markers form primarily a monolayer within the second deformable layer. Preferably, the beads are embedded in the substrate rather than coated onto the surface of the substrate. In one embodiment, the color B beads may be distributed throughout all deformable layers, as they can provide deformation information in three dimensions. Alternatively, a single layer of gel with beads embedded in the gel or adherent to the surface of the gel can replace the multiple gel layers. For example, the platform for biological assays comprises a base substrate providing structural support to the platform and at least one surface of the base substrate coated with position markers and a deformable layer positioned on top of the base substrate, wherein the deformable layer comprises a plurality of detectable deformation markers embedded throughout and/or adherent to an exposed surface of said deformable layer.

Implementations of the platform may also provide one or more of the following features. A top plate is positioned on top of the second deformable layer, wherein the top plate comprises multiple through-holes forming multiple wells on the platform. Bottom surfaces of the multiple wells may be coated. Coatings may include electrostatic treatments, hydrophilic or hydrophobic treatments, or coatings with a variety of specific proteins which can be adhesive. Specific regions of coatings are formed on the outer surface of the second deformable layer.

In another aspect, the disclosure provides a platform for biological assays, the platform including a base substrate providing structural support to the platform, at least one surface of the base substrate coated with fluorescent beads of a first color, a first deformable layer positioned on top of the base substrate, the first deformable layer primarily made of PDMS, with a stiffness less than 10 kilopascal (kPa) and with a thickness of about 50-300 μm, a second deformable layer positioned on top of the first deformable layer, the second deformable layer primarily made of PDMS, with a stiffness less than 10 kPa (likely identical to the first deformable layer) and with a thickness of about 1-5 μm, and embedded with fluorescent beads of a second color, wherein the fluorescent beads of a second color form primarily a monolayer within the second deformable layer, and a top plate positioned on top of the second deformable layer, wherein the top plate comprises multiple through-holes forming multiple wells on the platform with the deformable bead layer comprising the bottom of these wells. PDMS is impermeable to water, therefore reagents do not flow and mix between wells. Each well is independent from other wells in the platform. In an alternative embodiment, each layer is applied to each well of a standard multiwell tray. Multiwell format permits simultaneous traction force measurements of each well comprising different biochemical conditions. In preferred embodiments, the systems and platforms do not contain polymeric pillars or towers to detect cell movement or substrate deformation.

In yet another aspect, the disclosure provides a method of making a platform for biological assays, the method including providing a base substrate, coating the base substrate with position markers, forming on the base substrate a first deformation layer, and forming on the first deformation layer a second deformation layer embedded with deformation markers.

Implementations of the method of making a platform may provide one or more of the following features. A thin layer of position marker beads are applied in solution where the solvent is allowed to evaporate, or the beads are spin coated via liquid deposition onto the substrate. The step of forming the first deformation layer includes depositing a liquid or semi-liquid material onto the base substrate and then curing the liquid or semi-liquid material to form the first deformable layer. The step of forming the second deformation layer includes depositing a liquid or semi-liquid material onto the first deformation layer and then curing the liquid or semi-liquid material to form the second deformable layer. The thickness of both deformation layers can be precisely controlled by the amount of uncured material added, its viscosity, and spin-coating procedures.

Implementations of the method of making a platform may also provide one or more of the following features. The method includes functionalizing surface. The method includes binding a top plate on second deformable layer, wherein the top plate comprises one or more through-holes forming one or more wells on the platform. The method includes coating the bottom surface(s) of the one or more wells with selective proteins or chemical treatments. The method includes forming one or more islands of adhesive protein on the second deformable layer. In an alternative embodiment, each layer is applied to an independent well in a standard multiwell tray.

The substrates are characterized by physiological substrate stiffness, long shelf life (months to years), ease of storage and shipment (stored and shipped dry), ease of handling, cost-effective manufacturing, and readily functionalizable gel surfaces. The assay formats lend themselves to high throughput screening applications. Biological applications are numerous and some examples include cell culture, cell growth/proliferation, stem cell differentiation, cell stretch, cell migration, monolayer permeability, and measurement or monitoring thereof. The systems are useful to study and characterize cell behavior and cell function as these parameters pertain to pathophysiology, genetics, and drug discovery.

For example, a method of identifying an agent that alters cell traction force is carried out by culturing a cell on the platform described above in the presence and absence of a test compound, detecting a deformation of the second deformable layer by measuring a change in a position of a deformation marker, wherein the change indicates that the test compound alters cell traction forces. Detection of a plurality of changes in positions of markers generates a traction map. A comparison of the amount of deformation (i.e., changes in the positions of deformable markers) indicates whether or not the test agent induces a change in movement, e.g., migration, of the cell. Absolute traction or differential traction is determined using microscopy. Such data is useful to determine whether a test agent has therapeutic activity to affect physiological processes, e.g., immune activation, embryonic development, or cancer growth or metastasis. In one example, a reduction in the motility of a cancer cell in the presence of the test agent compared to in its absence indicates that the agent has anti-metastatic activity. In another example, airway smooth muscle (ASM) cells are cultured in the presence and absence of a test agent to identify an anti-asthmatic drug. Compounds that reduce ASM contraction as measured by a reduction in deformation of detectable markers in the presence of the test agent compared to in its absence indicate that the agent is useful to reduce bronchoconstriction in asthmatic conditions. In another example, endothelial monolayers are cultured in the presence and absence of test agents to assess their barrier protective capabilities. Those agents that reduce endothelial contractility, measured as a reduction in traction forces in the monolayer, confer barrier protective capabilities. In yet another example, fibroblasts with siRNA mediated knockdowns of specific protein tyrosine kinases and transfected with YFP paxillin are cultured sparsely. Their characteristics of adherence, spreading, and polarization are studied through spatiotemporal changes of traction forces, cell morphology, and focal adhesion size/area/orientation.

Many types of cells are analyzed using the systems described. For example, the cells are contractile or motile cells. For example, the cells are myosin-containing cells. Contractile cells such as muscle cells include skeletal muscle cells as well as smooth muscle cells such as airway smooth muscle cells, cardiac smooth muscle cells/cardiomyocytes, gastrointestinal smooth muscle cells, or myofibroblasts. Other examples include metastatic cancer cells as described above as well as motile immune cells such as macrophages and dendritic cells. The resulting findings have implications for understanding morphogenesis, differentiation, and development in health and in disease.

For example, a screening assay system comprises an airway smooth muscle cell and test compounds comprise candidate anti-asthma drugs. The screening method involves measuring the amount of cell-mediated deformation as described above and further comprises calculating root mean square values of absolute traction forces before and after adding the test compound. A drug-induced reduction in cellular traction force in the presence of the test compound indicates that the test compound relaxes airway smooth muscle cells and therefore is useful as an anti-asthma activity.

The platform is in the form of a slab format with the top plate comprising multiple through-holes forming multiple wells or in the form of a microtiter plate format, e.g., one that comprises a 6, 24, 96, 384 or 1536 well format, each well of which comprises a base substrate and deformation layers as described above. The platform can include two or more wells, such as 10, 50, 100, 2000 or any number between.

In yet another aspect, the disclosure provides a method of performing traction force microscopy on a platform for biological assays, including measuring cell-exerted displacement fields on a deformable layer of the platform, calculating cell traction fields from the displacement fields, and computing contractile responses of cells from the cell traction fields.

Implementations of the method of performing traction force microscopy may also provide one or more of the following features. The measuring step comprises capturing images of position markers in the platform. The images are captured before treatment and after treatment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting Other features will be apparent from the following description of examples, and from the claims. All references cited herein are incorporated by reference.

DETAILED DESCRIPTION

The physical environment of a living cell may affect the cell's ability to proliferate, metabolize, differentiate, and remodel. Living cells specify lineage and express different phenotypic and physical states in response to stiffness of their underlying platforms. For example, when cultured on a soft platform (e.g., 100 pascal (Pa) to 1 kilopascal (kPa), in the approximate stiffness range of brain tissue), stem cells express a neurogenic phenotype; when cultured on an intermediate stiffness platform (e.g., 8 to 17 kPa, in the approximate stiffness range of muscles), stem cells express a myogenic phenotype; and when cultured on a even stiffer platform (e.g., 25 to 40 kPa, in the approximate stiffness range of collagenous bone), stem cells express an osteogenic phenotype.

The traction force exerted by a living cell on the underlying platform is considered one important characteristic of the cell's biophysical states. Traction Force Microscopy (TFM) is used to analyze the traction force.

A multiwell format includes a stiff silicone, e.g., PDMS or acrylic, block with well holes is stacked on top of a layer of soft silicone, e.g., PDMS, which optionally includes fluorescent beads or other detectable markers for deformation tracking, which assembly in turn sits on top of a glass or plastic substrate. Unlike earlier approaches, this system (Cytoply™) permits force mapping, amplitude control, timing control, uniaxial or biaxial isotropic measurement, tensile or compressive properties, tenability of substrate (e.g., within physiologic ranges) and ease of scale-up to high throughput capabilities.

Platforms for Biological Assays

Figure 1:
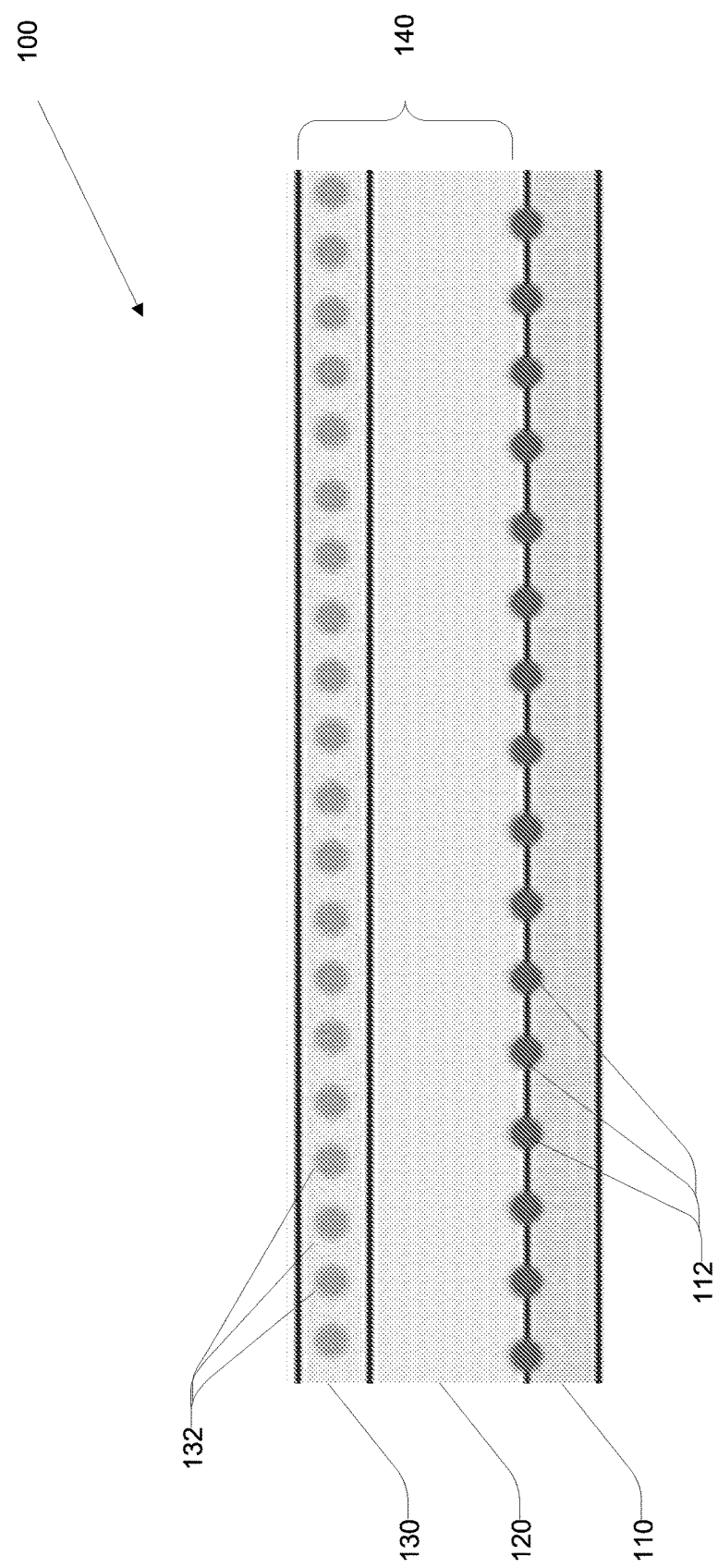
FIG. 1 is a side view illustration of an embodiment of a platform for biological assays.

A platform for biological assays disclosed in this document can contain multiple layers. FIG. 1 illustrates a side view of one example platform for biological assays. For example, a platform 100 can contain a base substrate 110, a first deformable layer 120, and a second deformable layer 130. The base substrate 110 can help to provide structural support to the platform 100. At least one surface of the base substrate 110 can be coated with position markers 112. The first deformable layer 120 can be positioned on top of the base substrate 110. The second deformable layer 130 can be positioned on top of the first deformable layer 120. Deformation markers 132 can be embedded in the second deformable layer 130.

The dimensions of layers and features depicted in FIG. 1 are for illustration purpose only and not necessarily to the scale. In one example, the base substrate 110 can be made of glass or other stiff materials (e.g., plastics, etc.) and can have a thickness of about 1 mm. Various materials with various dimensions can be used as position markers to coat the base substrate 110. For example, a layer of 800 nm fluorescent beads can be coated on one surface of the base substrate 110 as position markers.

Various materials with different Young's modulus (tensile elasticity) can form the first deformable layer 120. For example, the first deformable layer 120 can be primarily made of a polymer material. One example polymer material for the first deformable layer is PDMS. PDMS material possesses several attributes, e.g., generally inert to most aqueous reagents; generally insensitive to osmotic pressure; generally not poroelastic; can be stored dry at room temperature with a long shelf life (e.g., months or longer); easy and cost-effective to manufacture, handle, store, and transport; good surface spreading characteristics; good optical qualities; and readily functionalizable surfaces, etc. PDMS material can also have highly tunable stiffness. Via various mechanisms (e.g., varying polymer mass, changing cross-linking pattern and/or density, or adding supplemental ingredients, etc.), the stiffness of PDMS can be adjusted in the range from 0.1 kPa to 1 megapascal (MPa). As a comparison, traditional glass or plastic plate surfaces have stiffness in the range of gigapascals. Depending on the intended use, the stiffness of PDMS can be tuned to different desired physiological range (e.g., 100 Pa-100 kPa). In one example, the stiffness of the first deformable layer 120 can be less than 10 kPa.

The first deformable layer 120 can have various thicknesses. In one example, the first deformable layer 120 can have a thickness of about 50-200 µm. A layer of deformable materials with such a thickness range can help to mechanically de-couple upper layer(s) (e.g., the second deformable layer 130) from the base substrate 110 which can be stiffer to provide support for the device. In particular, the mechanical de-coupling can help to shield the biological assays (e.g., living cells) adhered to the surface of the upper layer(s) (e.g., the second deformable layer 130) from the effect of the potentially stiff surface of the base substrate 110.

The second deformable layer 130 can be made of the same material as that of the first deformable layer 120 or can be made of a different material from that of the first deformable layer 120. In one example, PDMS with stiffness in a desired physiological range can primarily form the second deformable layer 130. In another example, the stiffness of the second deformable layer 130 is less than 10 kPa. Various materials with various dimensions can be used to form the deformation markers 132 embedded in the second deformable layer 130. In one example, a layer of 800 nm fluorescent beads can be embedded in the second deformable layer 130. In some examples, the deformation markers 132 can have at least one different optically-distinguishable characteristic (e.g., fluorescent color, size, index-mismatch, reflectivity, etc.) from the position markers 112. For example, the position markers (fiduciary markers) 112 can be fluorescent red while the deformation markers 132 can be fluorescent green. The different fluorescent color can help to distinguish the position markers 112 coated on the base substrate 110 from the deformation markers 132 embedded in the second deformable layer 130. The position markers 112 coated on the base substrate 110 can be used to track the position of the platform 100. The deformation markers 132 can be used to track the deformation of the second deformable layer 130. The deformation of the second deformable layer 130 can be induced by traction force exerted by biological assays (e.g., cells) adhered to the surface of the second deformable layer 130.

The second deformable layer 130 can have various thicknesses. In one example, the second deformable layer 130 can have a thickness of about 1-5 µm. A layer of deformable materials with a thickness of about 1-5 µm can help the deformation markers 132 embedded in the second deformable layer 130 to form primarily a single layer. A 2-D monolayer of deformation markers 132 embedded in the second deformable layer 130 can help to make it easier and more accurate to detect and track the displacement of individual deformation markers. In addition to substrate stiffness, cells can also sense substrate thickness. (More details can be found in "Mechanosensing of substrate thickness" by Y. C. Lin, D. Tambe, C. Y. Park, M. R. Wasserman, X. Trepat, R. Krishnan, Guillaume Lenormand, Jeffrey J. Fredberg, James P. Butler, *Phys. Rev.* E 82, 041918 (2010), published Oct. 22, 2010, which is herein incorporated by reference in its entirety.) In order to measure these thickness dependent responses, deformation markers are dispersed throughout the deformable layers 120 and 130. Changes in deformation marker displacement can then be tracked through the thickness (3-D deformation).

When the first deformable layer 120 and the second deformable layer 130 are primarily made of the same material, the two layers can be combined and merged into one indistinguishable deformable layer 140 with deformation markers 132 embedded near its outer surface (the surface facing away from the base substrate).

Figure 2A:
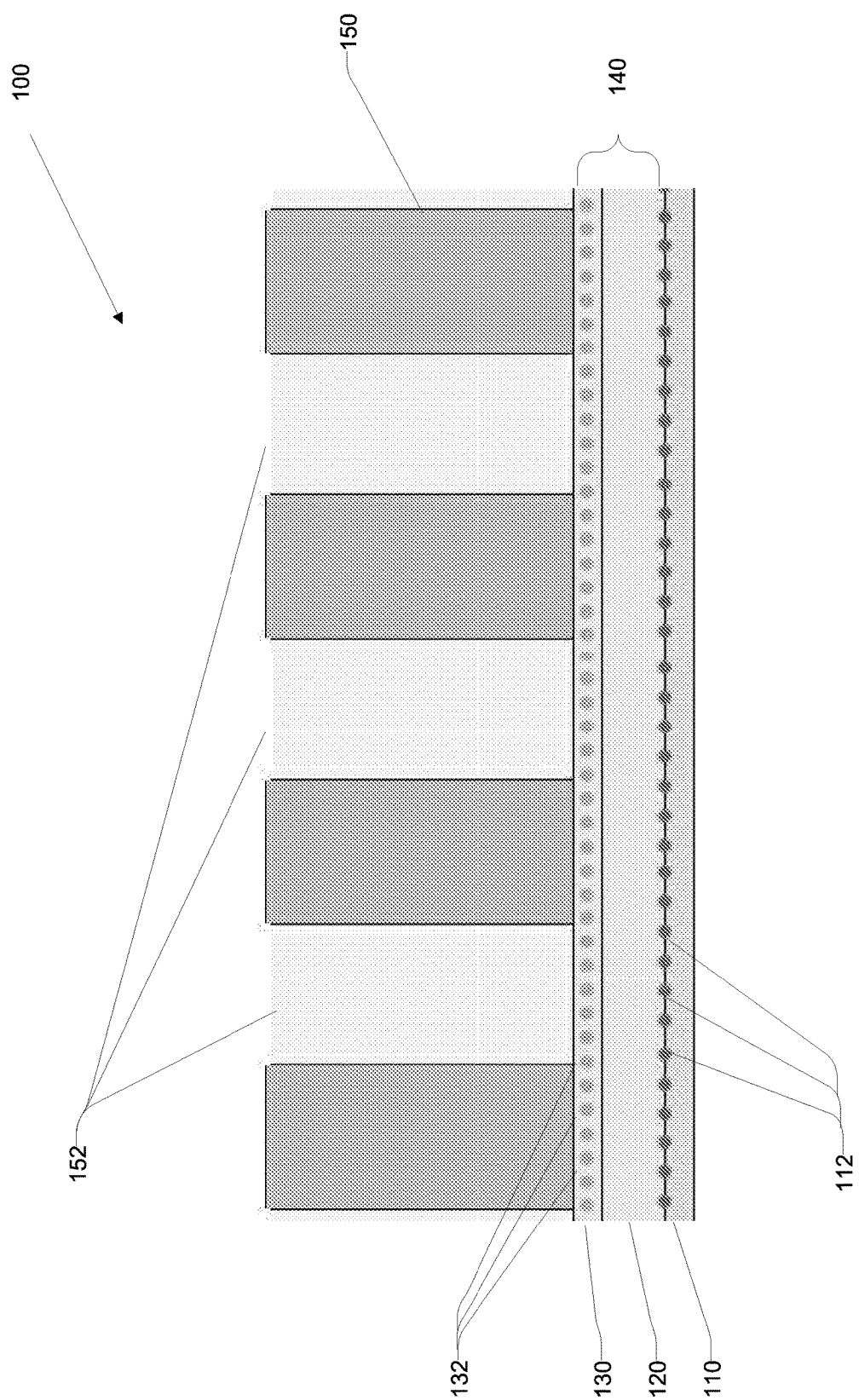
FIG. 2A is a side view illustration of another embodiment of a platform for biological assays.

Referring now to FIG. 2A, platform 100 can also have a top plate 150 positioned on top of the outer surface (the surface facing away from the base substrate) of the second deformable layer 130. The top plate 150 can be made of various materials, such as PDMS, acrylic, ABS, etc. The top plate 150 can also contain one or more through-holes 152. When bound on top of the second deformable layer 130, the one or more through-holes 152 in the top plate 150 can effectively form one or more wells 152 for hosting biological assays (e.g., living cell), with the bottoms of the one or more wells 152 being the outer continuous surface of the second deformable layer 130. The number of wells (e.g., 6, 12, 36, 72, 96, 384, etc.), the size and shape of each well (e.g., with a radius of 2 mm, etc.), and/or the arrangement of wells can be arbitrary and can be configured according to the intended usage and environment. The multiple wells can allow multiple biological assay analysis simultaneously, achieving high throughput. The monolithic fabrication can help to ensure uniformity across multiple wells. The multiple wells can also be independent to each other, allowing distinct cell media and biochemical conditions in different wells simultaneously. In an alternative embodiment, each layer is applied to an independent well in a standard multiwell tray.

Figure 2B:
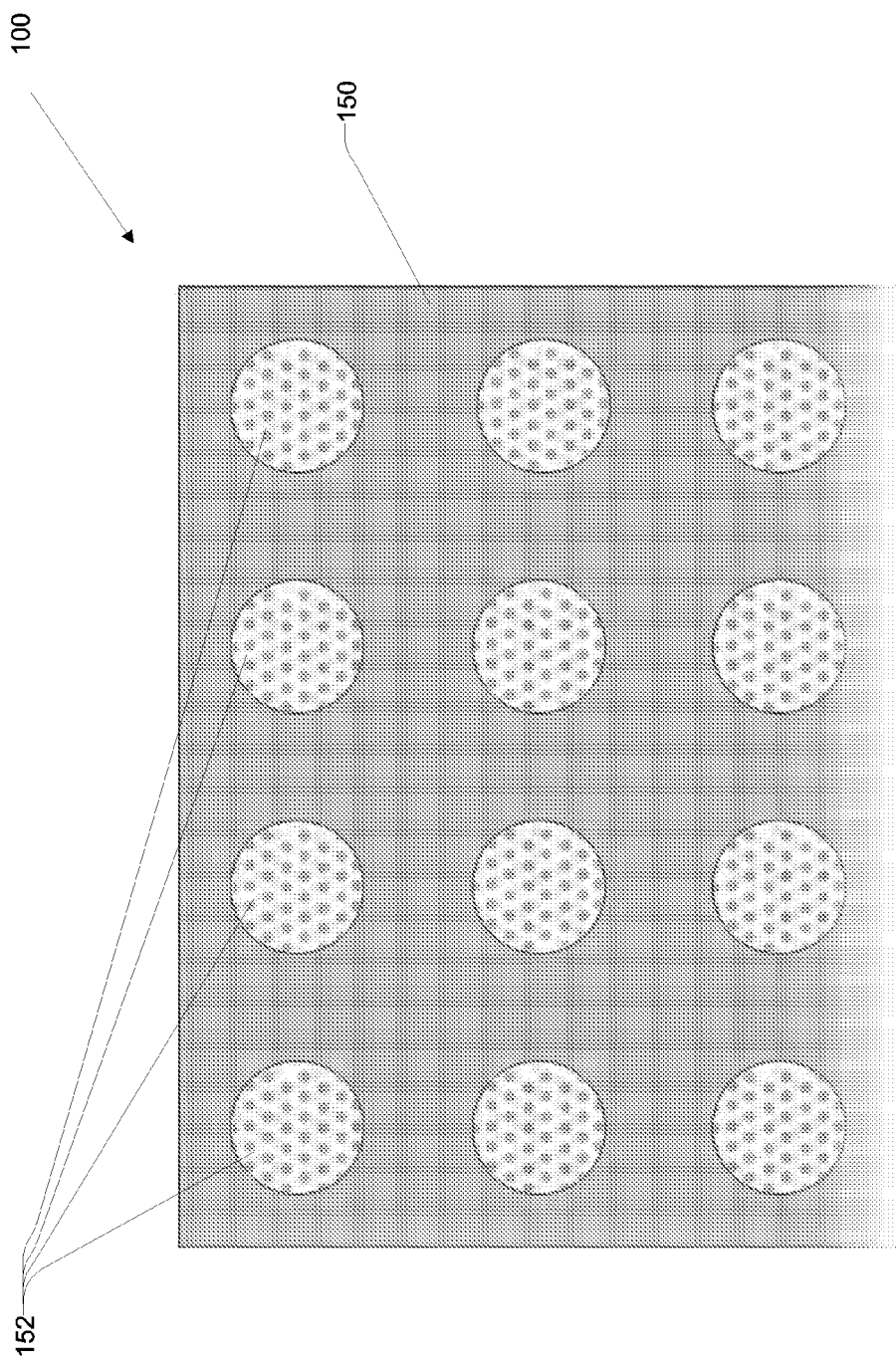
FIG. 2B is a top view illustration of the embodiment shown in FIG. 2A.

The top plate 150 can be made of various materials. In one example, the top plate 150 is made of a water-impermeable material, which can help to prevent cross-contamination from cell media in one well permeating through the well wall and into the cell media of another well. In another example, at least one of the first and second deformable layers can also be made of a water-impermeable material, e.g., PDMS, which can help to prevent cross-contamination among wells. Before the cell media is placed into a well, proteins or other coatings can be placed uniformly or in a patterned fashion on the bottom of the well. The protein can be adhesive (e.g., collagen, fibronectin, etc.). FIG. 2B shows a top view of platform 100 of FIG. 2A, illustrating the multiple wells formed on the outer surface (the surface opposite from the base substrate) of the platform 100.

Alternatively, one or more regions of adhesive protein or coating can be configured on the outer surface of the second deformable layer 130 prior to top-plate mounting. Proteins and coatings can also be applied in a discontinuous way such that patterns of adhesive and repulsive regions present themselves as a cell substrate. These regions of adhesive protein can effectively form multiple islands for hosting biological assays (e.g., cell media) on a continuous surface. The number of islands, the size and shape of each island, and/or the arrangement of islands can be arbitrary and can be configured according to the intended usage and environment. The multiple islands can allow multiple biological assay analysis simultaneously, achieving high throughput. The multiple islands can also be independent from each other, allowing distinct cell media and biochemical conditions in different wells simultaneously.

The dimensions of the platform 100 and each layer within can be independently controlled and configured according to the intended usage and environment. In one particular example, the platform is 5 cm wide, 7.6 cm long, and 0.6 cm thick, with 72 independent wells with radii of approximately 0.2 cm. (See, e.g., FIG. 4.)

Methods of Making Platforms

Figure 3:
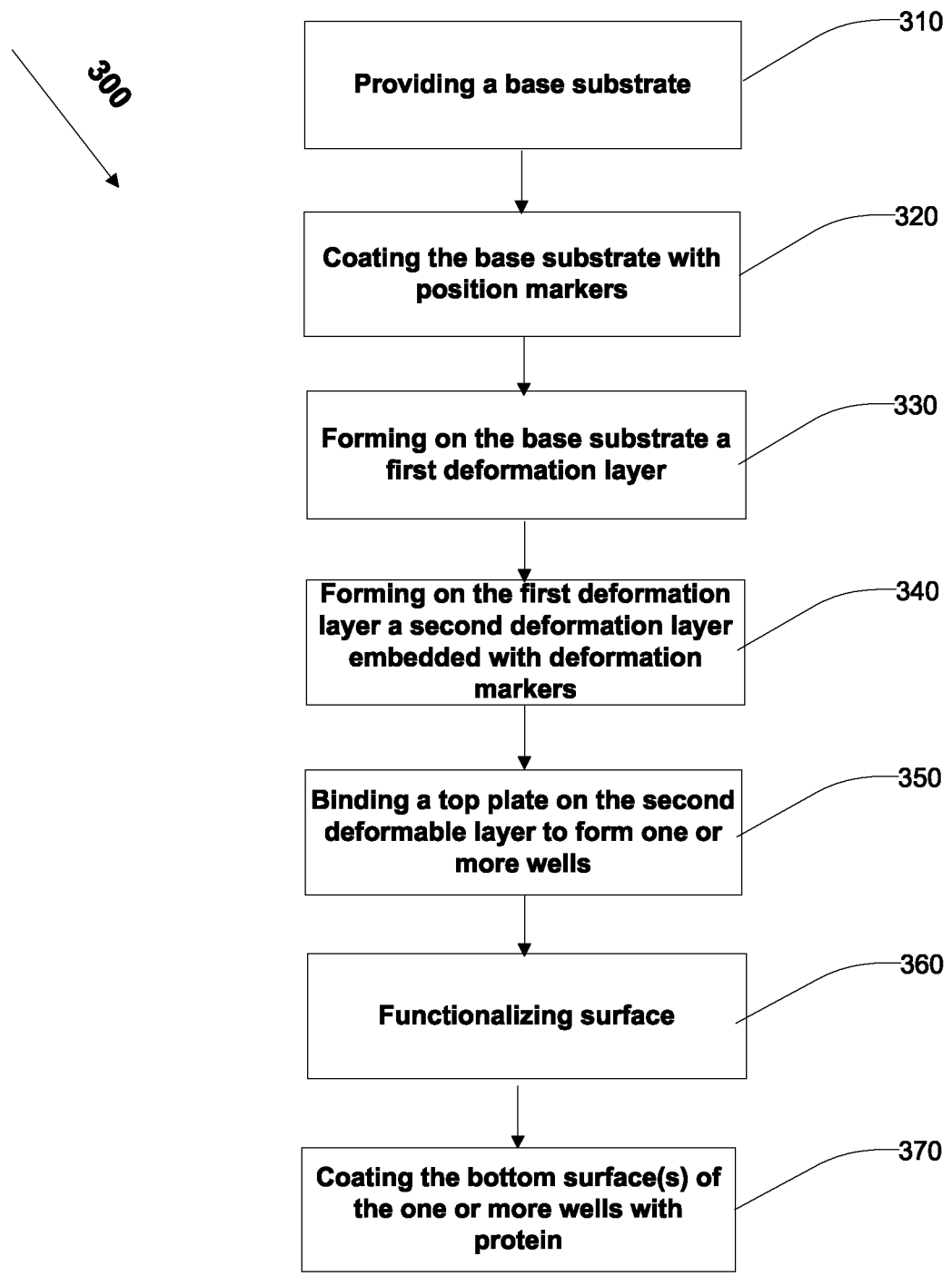
FIG. 3 is a flow chart illustrating the steps of one example process of making a platform for biological assays.
Figure 3A:
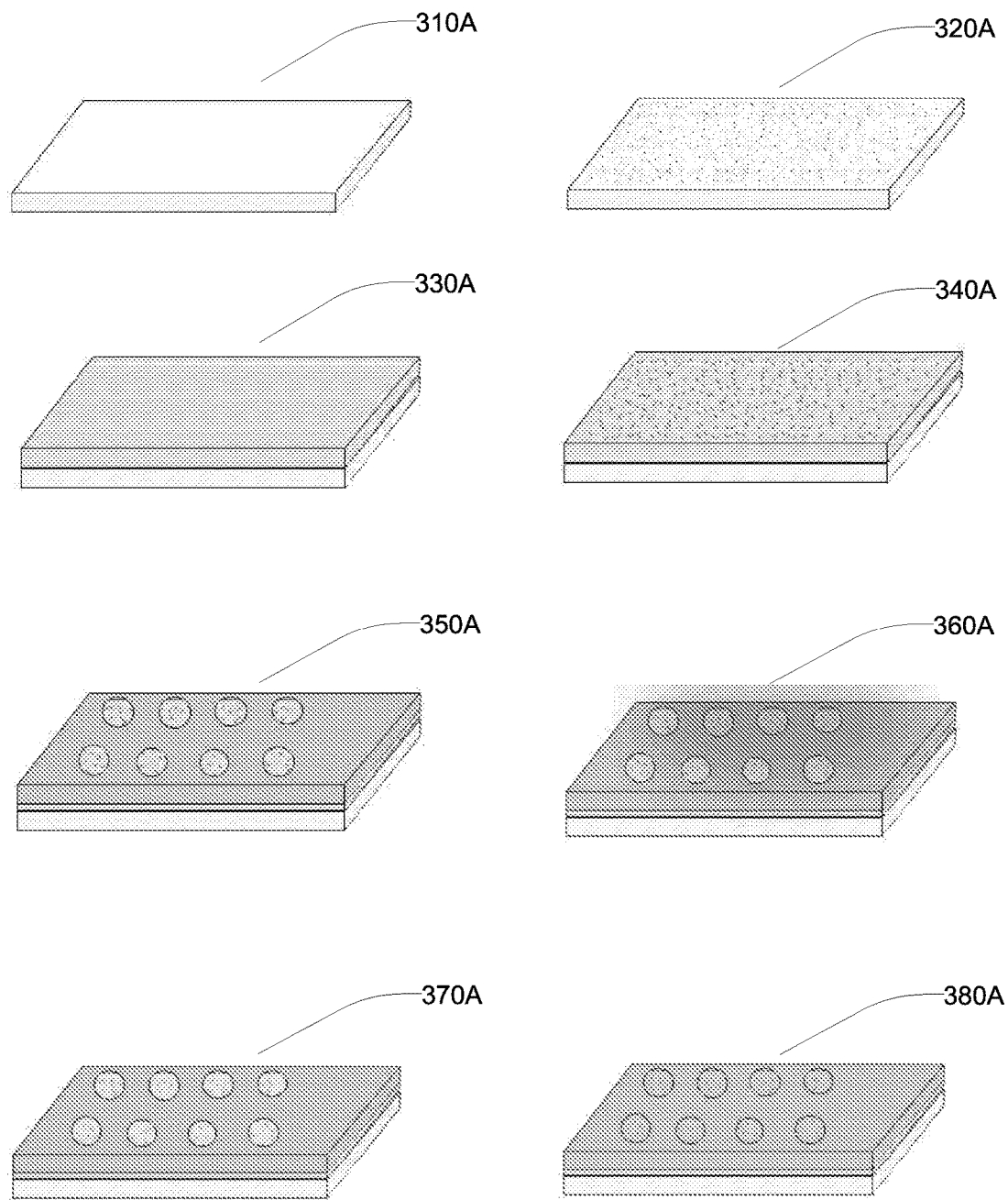
FIG. 3A further illustrates the steps described in FIG. 3.

One example process 300 of making an example platform for biological assays is illustrated in FIG. 3 and FIG. 3A. At first, a base substrate (e.g., a glass slide) is provided at step

310. An illustration of the example platform after step 310 is at 310A in FIG. 3A. Next, at step 320, the base substrate is coated with position markers. The position markers can be used to track the position of the platform. An illustration of the example platform after step 320 is at 320A. At step 330, a first deformable layer is formed on the base substrate. The first deformable layer can be first pre-formed then bound onto the base substrate. Alternatively, a liquid or semi-liquid material (e.g., polymer, PDMS, etc.) can be deposited onto the base substrate; a curing process can then follow to form the first deformable layer. An illustration of the example platform after step 330 is at 330A. At step 340, a second deformable layer embedded with deformation markers is formed on the first deformable layer. The deformation markers can be used to track the deformation of the second deformable layer. The second deformable layer can be first pre-formed with embedded deformation markers then bound onto the first deformable layer. Alternatively, a liquid or semi-liquid material (e.g., polymer, PDMS, etc.) with pre-mixed deformation markers can be deposited onto the first deformable layer; a curing process can then follow to form the second deformable layer. In either case, the thickness of the deformable bead layer can be set by the viscosity of the uncured mixture, and the centrifugal forces during spin coating. Alternatively, an extremely low viscosity uncured solution may be poured onto the surface and surface tension alone can spread the solution on a wettable surface. An illustration of the example platform after step 340 is at 340A.

The example process 300 can also include step 350, where a top plate is bound on the second deformable layer. The top plate can have one or more through-holes, effectively forming one or more wells for hosting cell assays. An illustration of the example platform after step 350 is at 350A. The top plate can be created, for example, from plastic with standard multiwell geometries. In another example, the top plate can be prepared from PDMS by making a multiwell plate scaffold (e.g., 2, 6, 96, 384, 1536, etc) from plastic. Using the scaffold as a mold, a negative of agarose can be prepared. Using the agarose as a mold, a positive of PDMS can be prepared. In on preferable embodiment, the positive of PDMS is in Sylgard. The positive PDMS can be cured (e.g., for 2-3 days) and peeled from the agarose. The example process 300 can also include a step 360 of functionalizing surface (e.g., coating or stamping with adhesive proteins such as collagen, fibronectin, laminin, and polylysine. In one example, the second deformable layer (e.g., primarily made of PDMS) can be functionalized by oxidizing its surface. Plasma cleaning can make hydrophobic surfaces hydrophilic by exposing OH groups. Several methods of functionalizing can be commonly used. One way is to plasma-clean the surface with oxygen plasma, then immediately coat the surface with $dH_2O$ water coating until protein coating; another way is to expose the surface to high intensity UV with $dH_2O$ water coating, and store wet until protein coating; yet another way is to coat PDMS with piranha solution (3:1 sulfuric acid:hydrogen peroxide) for about 3 minutes.

In another example, the second deformable layer (e.g., when primarily made of polyacrylamide (PAA)) can be functionalized for protein adhesion through the following two example multistep processes: (A) Using Sulfo-Sanpah: 1) Pre-mix 0.2-0.4 mg of Sulfo-Sanpah in 30 µl of DMSO, then in 3 ml of 50 mM HEPES while protecting from bright light. 2) Rinse each PAA gel with 50 mM HEPES, and apply 0.5 ml of Sulfo-Sanpah solution to each cover slip. Allow to sit for 10-20 minutes in darkness. 3) Expose dish with UV lamp for 5 minutes. 4) Optionally repeat the last two steps. 5) Rinse with 50 mM HEPES, and Store in PBS. (B) Using Hydrazine Hydrate ("Bulk and micropatterned conjugation of extracellular matrix proteins to characterized polyacrylamide substrates for cell mechanotransduction assays." Damljanović V, Lagerholm B C, Jacobson K. Biotechniques. 2005 December; 39(6):847-51): 1) Cover gels with Hydrazine Hydrate for 2-24 hours. 2) Cover gels with 5% glacial acetic acid for 1 hour. 3) Immerse gels in bath of $dH_2O$ for 2 hour, changing the water after an hour. 4) Store in PBS. An illustration of the example platform after step 360 is at 360A.

Steps 350 and 360 need not be performed in order and can be re-arranged in different circumstances. The example process 300 can also include step 370, where the bottom surface(s) of the one or more wells is/are coated with protein. The protein can be adhesive (e.g., collagen). Alternatively, one or more regions of adhesive protein can be configured on the outer-surface of the second deformable layer to form one or more islands. An illustration of the example platform after step 370 is at 370A. 380A in FIG. 3A illustrates the sample platform after cell media is applied.

Another example process of making an example 96-well platform for biological assays is as follow: A base substrate (here, a rectangular glass slide (55 mm×75 mm×0.1 mm)) is cleaned with acetone, then with isopropanol, and finally coated with 0.5 µm red fluorescent beads (Fluospheres, Invitrogen). A first layer of PDMS (e.g., NuSil™ silicone) with an elastic modulus of 5.1 kPa and a thickness of approximately 300 µm is uniformly spread on top of the beads, covering the glass slide. The first PDMS layer is then incubated at 65° C. for 3 days in order to cure. A second layer of PDMS (NuSil) also with an elastic modulus of 5.1 kPa but with a thickness of approximately 1 µm is then spin-coated onto the first layer of PDMS. Pre-mixed into this second PDMS layer is a 1% volume fraction of ~800 nm size green-fluorescence stabilized PMMA microspheres. Microspheres or beads are made from poly(methyl)methacrylate (PMMA) and a detectable marker such as a fluorophore, fluorescein or rhodamine, and then coated with PDMS. Preparation of microspheres or beads is well known in the art, e.g., as described in Klein et al. 2003, Colloid Polym. Sci 282:7-13, hereby incorporated by reference.

In this manner, the final composite (the glass slide and the first and second PDMS layers) yields a platform with a surface layer of finely dispersed fluorescent beads. The composite is then incubated at 65° C. for 3 days in order to cure. Separately, a 55 mm×75 mm×10 mm slab of PDMS (Sylgard 183) with an elastic modulus of ~1 MPa is incubated at 65° C. for 2 hours to form a top plate. Following its polymerization, an array of equally spaced holes (5 mm diameter) is punched at regular intervals throughout the slab. Next, this patterned slab and the PDMS (NuSil) composite described earlier are both oxygen plasma-cleaned for approximately 10 seconds to oxidize their surfaces. The oxidized surfaces are then lightly pressed against one another to bond them together. Each hole from the patterned slab now functions as an individual well, with the soft NuSil PDMS at the bottom of the well. The wells are washed and then ligated with 100 µg/ml monomeric collagen (PureCol) diluted in PBS. The plates are then rinsed in PBS and sterilized with UV in preparation for Fourier Transform Traction Microscopy (FTTM).

Figure 4:
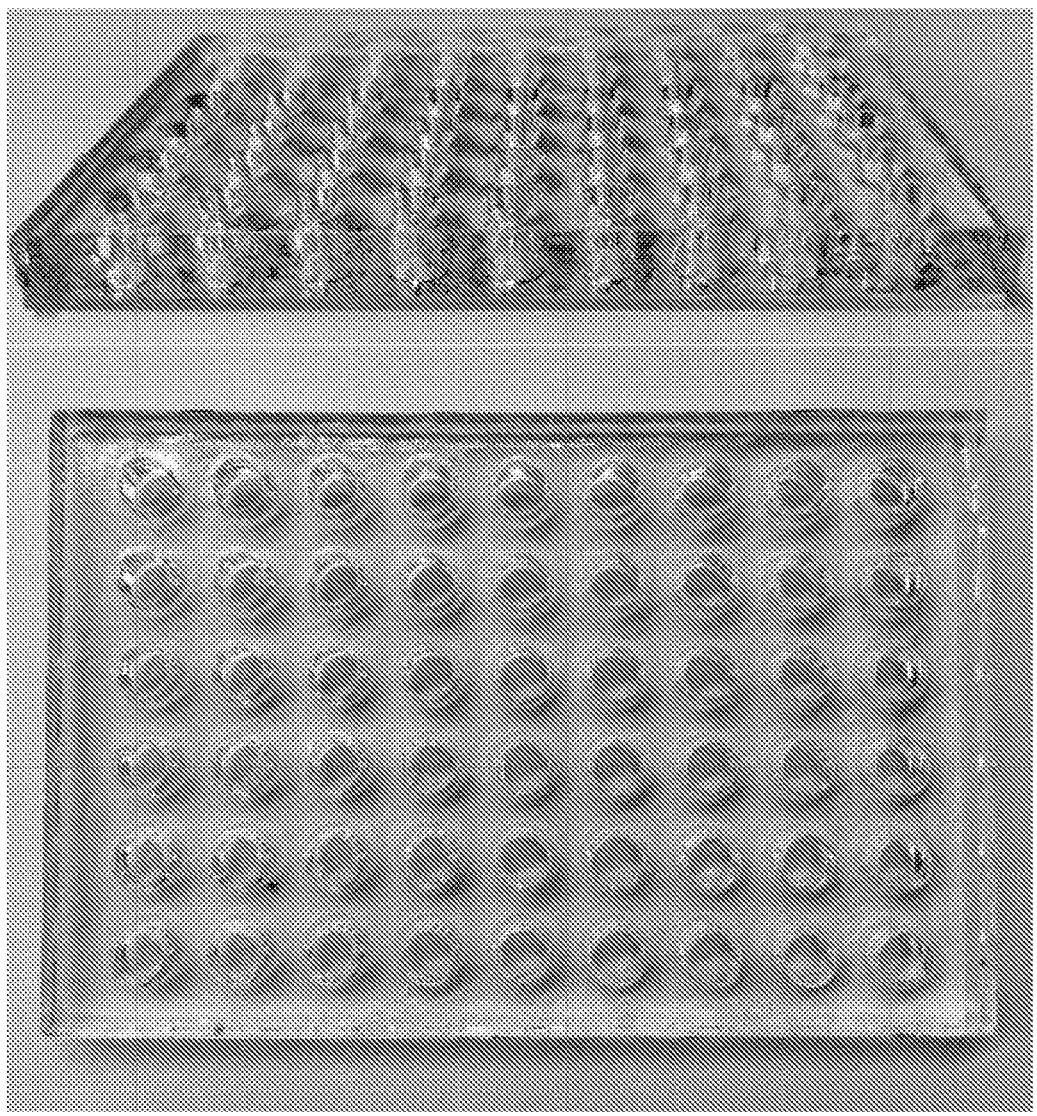
FIG. 4 contains pictures of an embodiment of a platform for biological assays.

Two pictures of an embodiment of a platform for biological assays from different perspective views are showed in FIG. 4. This particular sample platform is about 5 cm wide, 7.6 cm long, and 0.6 cm thick. It has 72 independent wells with radii of about 0.2 cm. All dimensions are independently controlled and can be set for a desired application.

Substrate Polymers

Various materials with different Young's modulus (tensile elasticity) can form the deformable layers. For example, polymer gels (e.g., hydrogel) have traditionally been used to form the deformable layers. Hydrogel is usually a natural or synthetic soft polymer with very high percentage of water by weight.

Hydrogels, such as polyacrylamide (PAA), have proven their utility as an adaptable and mechanically tunable substrate for studying traction forces, cell movement, and cell spreading. The stiffness of these hydrogels is determined by the concentration of polymer mass (acrylamide) and cross-linker (Bis-acrylamide), allowing a great degree of variability in mechanical properties. However, for the methods and compositions described herein, hydrogels have several disadvantages, which are tied to their high (e.g., >90%) water composition. For example, PAA is temperature, osmolarity, and pH sensitive, i.e., if the temperature, salt/ion concentration, or acidity of the solution around the PAA gel changes, the mechanical properties and even volume and shape of the gel will likely change by the osmotic pressure trying to equilibrate the concentration within the gel and surrounding solution as water moves in or out of the PAA gel. Thus, not only are PAA gels sensitive to such changes and should be prepared and measured under the same conditions they will be used, but any assay which changes these parameters will profoundly affect the hydrogel. Therefore, a PAA gel would be unsuitable to study the changes in cell traction force as a function of osmotic pressure, because not only the cell but the substrate itself would change. In addition, the water in hydrogels can evaporate, leading to changes in their properties. As a result, hydrogels must be kept cold and with 100% humidity, making them difficult to ship or store. Further, hydrogels are prone to contamination and easily colonized by fungi.

Due to these limitations of hydrogels, alternative materials were sought for compositions from which to fabricate the deformable layers. The alternative materials should be transparent and compliant yet water-impermeable. An exemplary alternative polymer material for forming the deformable layers is the silicone elastomer PDMS. Sylgard 184 is a commonly used PDMS in research. Although it is transparent and water-impermeable, it may be too stiff to be used to measure traction forces, as cells cannot measurably deform such a stiff material. A more compliant PDMS is made by NuSil™ (U.S. Pat. No. 5,620,773), and can be mixed and cured to have a stiffness comparable to that of PAA, and thus is suitable for cell traction force measurements. Such a compliant PDMS substrate combines the advantages of the PAA hydrogel (compliant, transparent) with that of an inert rubber (water-impermeable, stable at room temperature indefinitely) creating the ideal substrate for cell force studies, particularly those seeking high-throughput. By using a water-impermeable yet compliant substrate, a monolithic deformable substrate can be subdivided by a top plate with through-holes which is then bonded to the substrate, creating numerous wells. Since the substrate and top-plate are both water-impermeable, they can contain cells in different chemical/drug environments, allowing a programmable stage to rapidly scan over a large number of wells, and thus a large variety of drug concentrations and combinations. Such a device would be very difficult, if not impossible, to achieve using hydrogel.

But a smooth untreated elastomer (e.g., PDMS) surface can potentially have a physical characteristic of tackiness, that is, the characteristic of sticking to itself and other surfaces. Tackiness can be undesirable in some situations. For example, when PDMS is used to form the deformable layers in a platform for biological assays, high tackiness can add difficulty during manufacturing and handling and thus is generally undesirable. One method of modifying tackiness is by capping free polymeric PDMS brushes with a chemical such as tetramethyldisiloxane. Another way of reducing PDMS tackiness is to add hydrophilic silica fillers to the pre-curing PDMS dispersion, which can be configured to eventually displace PDMS at the surface. One example pre-curing PDMS dispersion comprises: (1) at least one crosslinkable polysiloxane, (2) silica filler, (3) crosslinking catalyst, and (4) a crosslinking agent. In some examples, the hydrophilic silica particles can have large specific surface area (e.g., about 75-200 square meters per gram) and density such that the hydrophilic silica particles float in the PDMS dispersion, that is, migrating to the top surface of the PDMS dispersion. This process is not limited to silica; it can be achieved with any colloidal particles which can be dispersed in PDMS during the uncured phase, and subsequently migrate to the surface whose tackiness is to be reduced. After curing, the silica particles are then securely imbedded within the top surface of the PDMS deformable layer with portions of the silica particles extending outwardly beyond the top surface, presenting a non-tacky textured surface of the PDMS deformable layer. The PDMS dispersion can be a two-part system, which requires mixing before curing, or a one-part system. Details in compositions of PDMS dispersions and methods of making can be found in U.S. Pat. No. 5,620,773, which is incorporated here by reference in its entirety. One example of commercially available PDMS dispersions is GEL-8100 from NuSil™ Technology LLC. GEL-8100 is a two-part system, comprising GEL-8100 Part A and GEL-8100 Part B. Part A and Part B are typically combined in a 1:1 ratio. Varying this ratio can change the mechanical properties: 1:1 yields ~1 kPa, 1:2 yields ~4.5 kPa, 1:5 yields ~12 kPa. To increase the stiffness alternatively, 1-3% by weight of Sylgard 184 (premixed 10:1 with its curing agent) may be added to the NuSil PDMS 1:1 mixture. Mixing Nusil 1:1:% Silgard yields 1:1:0 ~1 kPa, 1:1:1 ~2 kPa, 1:1:5 ~10 kPa, 1:1:10 ~25 kPa, 1:1:20 ~75 kPa. This broad range of tunable Young's moduli demonstrates the flexibility of the platform in providing a specified stiffness.

Traction Force Microscopy

Traction Force Microscopy (TFM) generally measures contractile forces exerted by biological agents (e.g., cells) on the platform surface to which they are adhered. TFM determines the contractile stress applied on the surface of a deformable platform with known mechanical properties by measuring the displacement of deformation markers embedded in the deformable platform. Deformation marker displacements are monitored by capturing images of the embedded markers in the deformable platform when a load is applied. The contractile stresses can then be calculated from the measured displacement and known elastic properties of the deformable platform.

One form of traction force microscopy is Fourier Transform Traction Microscopy (FTTM). In one example method, the measurements can be performed in three steps. First, the cell-exerted displacement field is measured. Next, the cell traction field is calculated from the displacement field. Last, the root mean square (RMS) value of overall ASM monolayer contraction is computed from the cell traction field.

One method of computing the displacement field is as follows: In each well of the multi-well plate, an image of the deformation markers near the surface and an image of the position markers at the bottom can be obtained in quick succession. Such time-lapsed image pairs can be registered at three different time points: before cell placing (reference), before treatment (basal), and after treatment (treated). By comparing the basal or treated positions of the deformation markers with their corresponding reference positions, the cell-exerted displacement fields can be obtained at pre-treatment baseline or after treatment. By comparing the basal or treated positions of the position markers with their corresponding reference positions, potential spatial drifts between image pairs of deformation markers can be corrected.

One method of computing the traction field is as follows: From the displacement field and from the platform stiffness and thickness, the monolayer traction field and the root mean squared (RMS) value of traction can be computed. The RMS values can be a quantitative measure of contractile response, and can be considered as a surrogate (cell-based) for the AHR phenotype.

If the reference image is eliminated, however, differential maps, instead of absolute traction maps, can be obtained. For minor drug effects, the difference map can disclose negligible traction forces. For major drug effects, however, the differential traction forces identified can be substantial. The current subject matter is not limited to differential traction maps, for example, absolute traction maps may be used.

Differential traction is a technique of measuring traction that includes using two images of fluorescent markers on/in an elastic substrate that contain cells on the substrate. The two images are taken before adding drug (baseline) and after adding drug and passage of a drug incubation time (e.g., 1 hour). By comparing the two images, one can measure a magnitude of the drug effects, although the process cannot determine whether the effect is increasing cell contraction or decreasing it.

Absolute traction is a technique of measuring traction that includes using three images, specifically, a before, an after, and a cell-free image. The first image is acquired with cell or cells on the elastic substrate and the second is acquired after cell or cells have been removed (e.g., using trypsine). The second image represents a stress free state of the elastic substrate. In the case of drug treatment, one can take another image after adding the drug while keeping the cells on the elastic substrate. In this case, one has three images (before, after, cell-free). By comparing before vs. cell-free and after vs. cell-free, one can calculate the absolute tractions by which cells are exerting on the elastic substrate at two time points (before and after adding drugs). By comparing the two determined tractions, the effect of drug can be determined including whether the traction of the cells increases or decreases.

Figure 5:
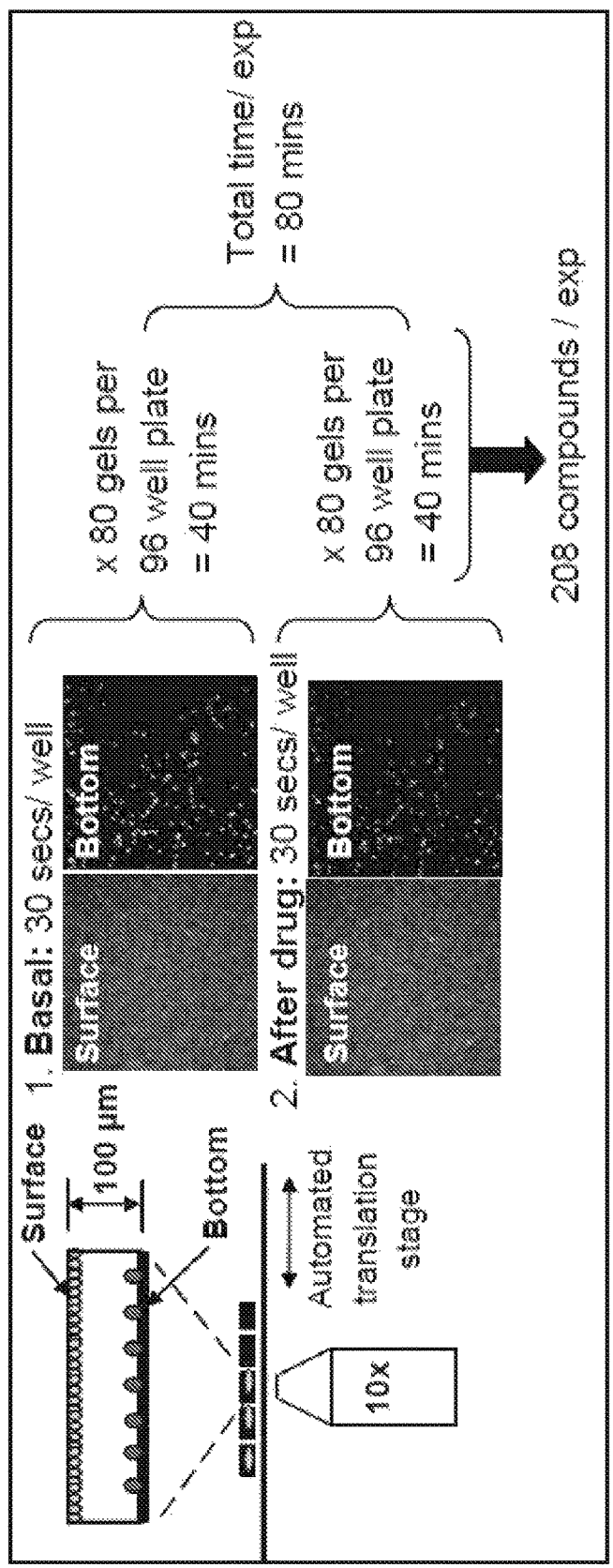
FIG. 5 illustrates an example experiment using high throughput traction force microscopy.

FIG. 5 illustrates an example experiment using high-throughput traction force microscopy. Fluorescent bead images can be acquired in pairs (surface and bottom beads). First, basal imaging can be performed for each well. Next, each well can be treated with a drug cocktail containing 8 compounds. Then, a second pair of images for the same well can be obtained after one complete pass across the 96-well platform (about 40 minutes). By the end of this example experiment, florescent bead images from 80 gel-wells would be obtained with a drug incubation time of about 40 minutes per well.

Figure 6:
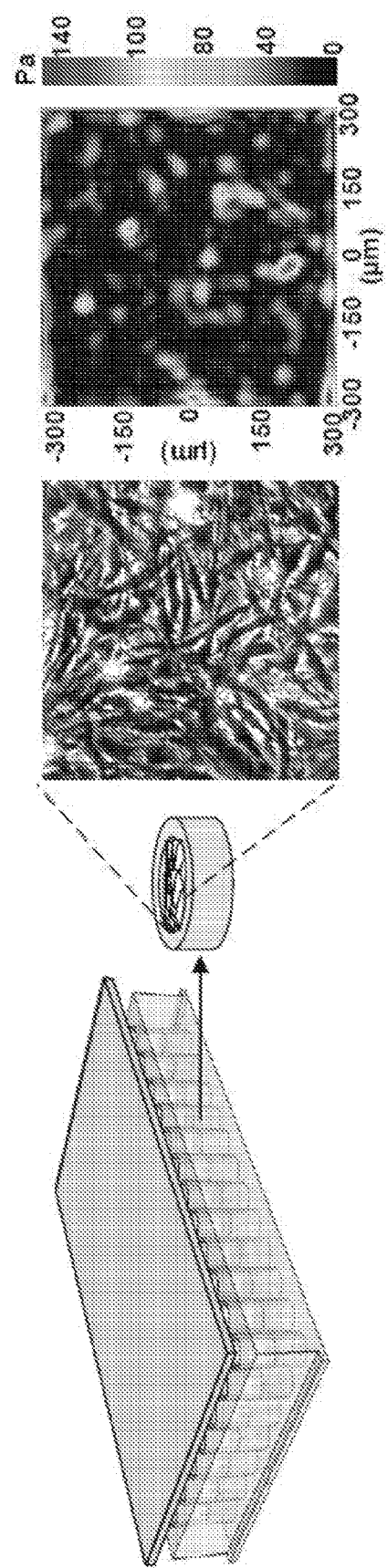
FIG. 6 illustrates an example configuration for high-throughput traction force measurements.

FIG. 6 illustrates an example configuration for high-throughput traction force measurements. Human ASM cells are placed as complete mono-layers on a collagen-coated 96-well gel platform. A representative basal phase contrast image and corresponding differential traction force map of the monolayer treated with 2.5 μM Y27632 are shown in FIG. 6. Colors indicate the magnitude of the tractions in Pascal.

Processing of Tracking Data

Some technical details of the methodology by which differential tractions can be assessed with the new platform are described here. We begin with the observation that as cells exert tractions on their substrate, the substrate itself deforms, and if this deformation is measured, then the tractions responsible can be deduced. This can be done in two independent steps.

First, the deformation of the substrate is characterized by the displacements $\vec{u}(x,y)$ induced on the surface, at the cell/substrate boundary. Here and in what follows, we assume that the cells or cell sheets in monolayers are sufficiently broad in the tangent plane that displacements normal to the substrate surface can be neglected. The displacements in turn are measured by differences in two microscopic images where beads or other fiducial markers, including intrinsic optical inhomogeneities of the substrate, suffice to deduce displacements of the substrate secondary to differential cell tractions in image pairs. These image pairs are, in this application, taken to be those with cells in a basal or control condition, and those same cells following treatment with a panel of contractile or relaxing drugs. The method by which these image pairs are compared and the substrate displacements are measured is through optimization of cross correlation of small windows spread throughout the field of view. Specifically, we compare the intensity map of each of the two images $I_0(x,y)$ and $I_1(x,y)$ by computing the function $<(I_0(x,y)-\overline{I_0}(x,y))(I_1(x+u_x,y+u_y)-\overline{I_1}(x+u_x,y+u_y))>$, where the overbar denotes average, and the expectation operator $<\bullet>$ denotes averages over each window, normalized by the variance of the intensity in each window. In words, each window in one image is compared with that same window, shifted by a variable displacement $\vec{u}(x,y)$. This gives rise to a correlation that is maximized when the window displacement corresponds to the displacement of the center of each window. In this way, the displacement field, $\vec{u}(x,y)$, on a subpixel by subpixel basis is computed.

Second, given the displacement field, it is in principle possible to compute the gradients of the displacements, which are the local strains, which by Hooke's and Navier's Laws, are proportional to the local substrate stresses. These are balanced by the tractions that the cells have exerted on the substrate. In practice we invoke the well known Boussinesq solution to the problem of the induced displacements on the boundary of a semi-infinite elastic medium, or on the boundary of a finite thickness slab (Further details can be found in "Mechanosensing of substrate thickness" by Y. C. Lin, D. Tambe, C. Y. Park, M. R. Wasserman, X. Trepat, R. Krishnan, Guillaume Lenormand, Jeffrey J. Fredberg, James P. Butler, *Phys. Rev.* E 82, 041918 (2010), published Oct. 22, 2010, which is herein incorporated by reference in its entirety), given a point source of traction on its surface. In particular, given a unit point source of traction $\vec{T}_0$ at $\vec{r}=0$ (in the two dimensional plane of the cell/substrate interface) the Boussinesq solution gives displacements $\vec{u}_0(x,y)$. In general, for distributed tractions $\vec{T}$, the displacement field is given by the convolution of the Green's function $\vec{u}_0(x,y)$ with $\vec{T}$, i.e. $\vec{u}=\vec{u}_0 \otimes \vec{T}$. The inverse problem is then the recovery of the traction field $\vec{T}(s,y)$ given the observed displacement field $\vec{u}(x,y)$. This is a difficult problem in (x,y) space, but yields to a particularly elegant solution in Fourier space (Further details can be found in "Traction fields, moments, and strain energy that cells exert on their surroundings" by Butler, J. P., Tolic-Norrelykke, I. M., Fabry, B. & Fredberg, J. J., *Am J. Physiol Cell Physiol* 282, C595-605 (2002), which is herein incorporated by reference in its entirety). Here the solution is exact in the sense of a discretized grid of pixels. Moreover, it is, for a given displacement field, not sensitive to noise—the condition number, roughly the ratio of the highest to lowest eigenvalues of the transformation matrices required to effect this solution, is equal to unity, implying that the Fourier procedures per se in this step neither magnify nor introduce noise. Finally, we note that our approach encompasses both single cell preparations, as well as monolayers of confluent cells, and those on micropatterned substrates.

Differential traction microscopy relies on the comparison of images both of which have cells present; one in basal or control conditions, and the other following treatment with individual or a panel of drugs. In absolute traction microscopy (as developed over the past decade), image pairs are compared with one devoid of cells, following e.g. trypsin treatment, which leaves the substrate in its native configuration of bead or other marker configurations. Differential traction microscopy improves throughput. The basal state of contractility of the cell cannot be measured, but it is indeed not of primary interest in the implementation of high throughput platforms that gauge changes in contractility. These changes in cell/substrate tractions that are measured through this new differential traction microscopy technique include those associated with individual or panel of pharmacologic interventions, stretch of the substrate (i.e. the mechanical milieu), among other possible interventions. The changes that can be detected with differential traction microscopy do not give a signed change to the difference in underlying tractions, compared with e.g. trypsinized cell free substrates. That is, differential traction microscopy can be advantageous because the magnitude of contractile changes can be assessed while avoiding a need for independent assessment of trypsinized image acquisitions, thereby enabling high throughput screening, drug discovery, with and without responses to independent modulation associated with mechanical stretch. While differential traction microscopy has been discussed herein, absolute traction microscopy can be used.

Example 1

Applications/Uses

Platforms for biological assays disclosed in this document can be widely used in many biology systems to study and measure the behavior and function of a variety of cell types. For example, the compositions, devices, and methods are used in cell culture, cell biology, cell growth, cell proliferation, stem cell differentiation, cell stretch, cell migration, pathophysiology, genetics, drug discovery, permeability, and studying cancer, asthma, fibrosis, hypertension, etc. or screening for compounds that affect the development and progression of such pathologies.

Soft, tunable, and elastic substrates are fabricated with tissue-like (physiological) stiffness, e.g., 1 kPa to 1000 kPa. The substrates are optionally fabricated in standard multicell configurations, e.g., 6, 12, 96, 384 (or more) well culture and represent precise, cost-effective and simple platforms that are easily adaptable to numerous screening formats. These formats may be designed for turnkey integration into existing multiwell automated systems, such as robotic pipetting systems, or modeled around any specified well shape, dimensions or number.

The systems are particularly useful for cell culture applications. In accordance with the invention, in vitro stiffness of the culture substrate corresponds to in vivo stiffness of tissues and organs in which cells reside in the body. Cells respond to the mechanical attributes of the culture medium. For example, in response to brain-like, muscle-like, or bone-like stiffness, a stem cell differentiates into a nerve, muscle, or bone cell, respectively.

Cell stretch is controlled in amplitude, timing, and in isotropy. Substrate stiffness is tuned over a wide range of stiffness. Cell contraction forces are measured directly in space and time.

Characterization of cell migration is relevant to numerous physiological processes such as cancer, morphogenesis, wound healing, and pattern formation. Cell monolayers, e.g., epithelial cells are cultured on substrates comprising physiological stiffness, and cell-to-cell and/or cell-to-substrate forces are measured directly. Cell-cell and cell-substrate forces are correlated with monolayer structure and molecular composition of the substrate. Cell velocity vectors align along principal stress ellipses.

In asthma, aberrant remodeling of the airway is initiated by humoral factors in the airway smooth muscle (ASM) microenvironment, but is perpetuated and amplified by changes in the ASM physical microenvironment. Soft substrates and active matrix stretch, as are found in normal airway physiology, are protective against aberrant remodeling. Experiments to evaluate human ASM growth/proliferation in response to stiffness were carried out. Human ASM cell number increased over 24 hours on both 400 Pa and 6400 Pa substrates. Strikingly, the application of stretch (10% amplitude, every 6 minutes) was most potent on physiological stiffness substrate (400 Pa), and attenuated the increase in cell number by approximately 75% ($p<0.05$). The inhibitory effect of stretch was largely diminished on the stiffer matrix (6400 Pa). Example 2 below further describes drug discovery approaches to identify compounds useful in the treatment of asthma.

Genome-wide association studies (GWAS) are used to identify common genetic factors that influence health and disease. By combining Cytoply™ and traction force microscopy with GWAS studies, genetic information is correlated with a cellular phenotype that is a direct measurement of airway smooth muscle cell function. Such integrated approaches represent a paradigm for genetic studies of asthma and other complex diseases.

The systems are also useful to study contractile forces that drive cell permeability. Substrate stiffening as occurs in diabetes, hypertension, cancer, atherosclerosis, and renal disease, enhances endothelial monolayer forces and promotes barrier disruption. Such forces are measured using the systems described above to study changes in cell contractile forces as a factor of disease progression and in response to compounds, e.g., in a screening assay to identify compounds that increase or decrease cell contractility induced paracellular permeability.

Example 2

High-Throughput Drug Screening Assay to Identify Compounds to Alleviate Bronchoconstriction in Asthma The devices, compositions, and methods described above are used to screen for the functional role of compound in alleviating bronchoconstriction in asthma. Interventions, which disrupt actin-myosin-actin connectivity in human airway smooth muscle (ASM) cells also reduce ASM contraction, and thus limit bronchoconstriction in asthmatic conditions Bands of submucosal smooth muscle course throughout the conducting pulmonary airways, wrapping circumferentially around the airway. Like a boa constrictor squeezing its prey, these muscle bundles constrict the air-way lumen when they contract. Bronchoconstriction of a modest degree can occur transiently in normal air-ways, but in asthma the bronchoconstriction is abnormally exaggerated and prolonged. The resulting airflow obstruction increases the work of breathing, deranges the distribution of ventilation, and in its most severe manifestation leads to ventilatory failure and death. Given its central role in asthmatic airflow obstruction, ASM contraction has long received attention as a therapeutic target, with strategies directed at relaxing ASM (e.g., 32-adrenergic agonists) or at ablating ASM altogether (e.g., bronchial thermoplasty).

The compositions and methods are used to identify compounds to relieve airflow obstruction in asthma. The strategy is to impair the ability of contracted ASM to remain shortened after contraction has occurred. While ASM that has contracted against a steady load can remain shortened indefinitely, ASM contracting against a fluctuating load first shortens then relengthens—even while contractile stimulation is continued. When the fluctuating load is of physiological magnitude, this "force fluctuation-induced relengthening" (FFIR) can be quite substantial and can be further enhanced pharmacologically. In the intact lung, ASM is constantly exposed to force fluctuations imposed by tidal breathing. The key premise of the screening approach is that drugs targeted specifically to exaggerate breathing-induced FFIR should release ASM's squeeze on the airway lumen and thus relieve bronchoconstriction.

To screen hundreds, thousands, e.g., 12,000, or millions of compounds, cells are interrogated in multiwell gel plates. Human airway smooth muscle (HASM) cells are cultured in monolayers. For automatic drift correction, a bottom layer of beads is attached rigidly to the glass surface on the bottom side of the gel. Differential traction maps are generated. FIG. 6 shows a system for drug discovery in asthma. Human ASM cells are plated at confluence upon collagen-coated Cytoply™ plates. A representative basal phase contrast image is obtained before and after drug treatment. Colors show the magnitude of force in Pascal (Pa).

Preparation of multiwell gel-plates. Glass-bottom 96-well plates (Matrical) with 0.5 µm red fluorescent beads (Fluospheres, Invitrogen) adherent to the inner glass surfaces are treated with a 0.4% g-methacryloxypropyltrimethoxysilane (Acros Organics) to enable covalent attachment of acrylamide to the glass during gel polymerization. Solutions containing 0.075% ammonium persulfate, 0.15% tetramethylethylenediamine, and acrylamide:bisacrylamide and 0.2 µm yellow fluorescent beads are delivered into the well plate. A 96-pin block with affixed, hydrophobic glass squares corresponding to the diameter of the wells are inserted, sandwiching the polymerization solutions between two glass surfaces. Final gel thickness of 100 µm is obtained by placing 100 µm-thick spacers in the corner wells. Following polymerization, the block is removed freeing the apical surface, and the gels immersed in 0.5 mg/ml of the heterobifunctional crosslinker Sulfo-SANPAH diluted in 50 mM HEPES buffer, pH 8.5. After 5 min UV exposure, the crosslinker solution is removed and the gels rinsed once with HEPES buffer. Monomeric collagen (Pure-Col) diluted in PBS at 100 µg/ml is delivered to each well and the well is incubated for 4 hrs at room temperature. The well plate is rinsed in PBS and UV-sterilized prior to cell seeding.

Cell culture. Primary HASM cells are cultured densely (30,000 cells per well) to facilitate cell adhesion as a monolayer within a collagen island around the gel center.

Computation of the displacement field. Both the gel surface beads (from which the tractions are recovered) and the bottom beads attached to the well bottom (to correct for potential drift between image pairs of surface beads are imaged. Gel displacements are computed using correlation-based particle image velocimetry. To reduce systematic biases in sub-pixel resolution, peak-locking effects will be implemented as an iterative process (n=4 iterations) based on the continuous window shift technique.

Computation of the traction field—differential Fourier transform traction microscopy (FTTM). To measure drug responses using traditional FTTM, fluorescent bead positions are measured are three different times: at baseline, after drug addition, and after cell removal by trypsinization. This approach yields two absolute cell traction maps—one before and one after drug treatment. If the post-trypsinization image is eliminated, however, differential maps instead of absolute traction maps are obtained. For minor drug effects, the difference map discloses negligible traction forces. For major drug effects, however, the differential traction forces identified are substantial. These differential traction forces are further quantified by calculating net contractile moment. FIG. 6 shows an example of one such difference map.

Experimental protocol. Fluorescent bead images are acquired in pairs (surface and bottom beads). Following basal imaging in each well, the well is treated with a drug cocktail containing a plurality of compounds, e.g., 8 compounds, and a second pair of images from that same well is obtained after one complete pass across the 96 well plate (~40 minutes). In this manner, by the end of each experiment, florescent bead images from 80 gel-wells with a drug incubation time of 40 minutes per well have been obtained.

Throughput. On the first pass, 12,000 compounds are studied 8 at a time, with 3 replicates, each requiring 2 images, for a total of 9000 images, with another 1000 images required for positive (histamine) and negative (Y27632) control interventions and no-compound "blank" plates. Given a rate of two images per minute, the first pass of all 12,000 compounds requires 84 hrs with additional time for data processing and cell preparation. Wells with the 40 greatest responses would include 320 distinct compounds. On the second pass, these 320 compounds are then studied one at a time at each of 5 concentrations (1 nm to 10 µM) in 3 replicates, each requiring 2 images, which with control wells total approximately 10000 images, corresponding to an additional 84 hours at the bench. The method is easily scaled up using methods known in the art.

Example 2 describes a high-throughput assay for probing drug targets in asthma. The methods and general approach are applicable to any pathology where aberrant cellular mechanics play a central role. Exemplary pathologies include cancer, bladder dysfunction, glaucoma, bone remodeling, Age related Macular Degeneration, and abnormal angiogenesis. The system is also readily combined with techniques that impose mechanical stretch, e.g., WO 2009/032174 A1, hereby incorporated by reference.

Example 3

High-Throughput Screening Using Cellular Contraction as a Mechanical Endpoint

A characteristic of asthma is excessive contraction of airway smooth muscle. A high-throughput screening assay called high-throughput traction microscopy (HTTM) enables discovery of novel drugs that relax contracted airway smooth muscles.

Figure 9:
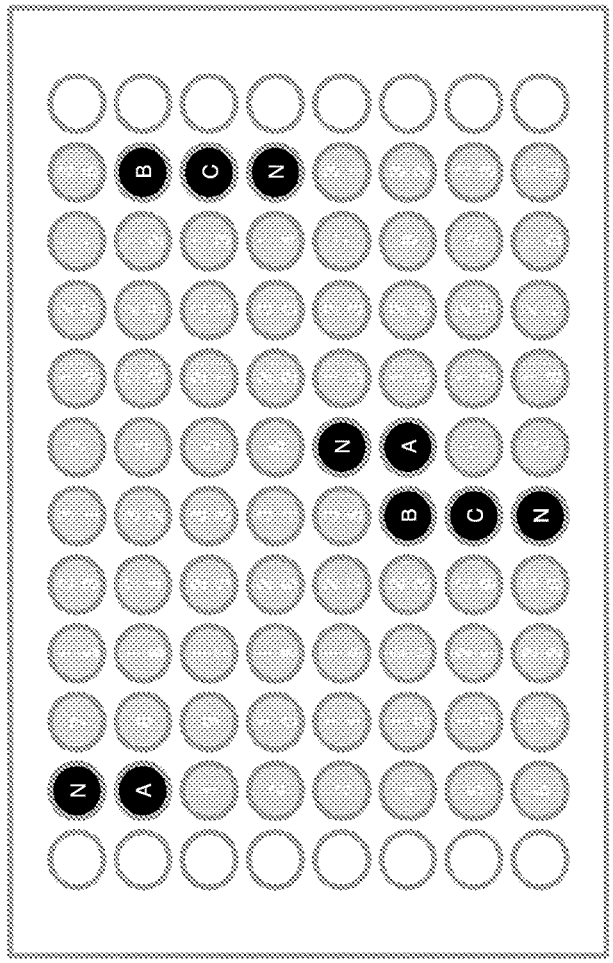
FIG. 9 illustrates an example layout of a multiwell plate.

Acrylamide gels with 1.8 kPa stiffness and 200-μm thickness were made in 96-well plates, fluorescent markers were coated in a single layer (0.2 μm) onto gel surfaces, and the gel plates were mounted on a fluorescent microscope with motorized stage. On each gel, HASM cells from a single donor were cultured to near confluence. Each well was seeded with 20,000 cells and was serum deprived for 2 days. FIG. 9 illustrates an example layout of a multiwell plate.

Imaging of the fluorescent markers included 10× magnification, at 37° C. Three rounds of imaging was performed per plate. For each imaging, two florescent images and one phase image was acquired. Since a common problem for circular shape dishes is rotation of wells, the multi-well plate is optionally a rectangular shape, so that one can easily find the same location in each well. Images of fluorescent markers in each well are taken before cell seeding. In addition, one can store the exact z-position of best sensor focus on each well. It is known that the multi-well plate may not be perfectly flat (e.g., there can be sagging in the middle of the plate). In addition, small changes in sensor depth focus can jeopardize image quality and in turn, traction calculation. Therefore, a prescanning step can aid in screening. After prescanning, wells are seeded with cells and a regular cell culture protocol can be followed. In example 3, a baseline-scanning typically takes fifteen minutes. Drugs can be added and the plates can be incubated for a certain time (e.g., in example 3, incubation occurred over a period of one hour). After incubation, a drug-scan can occur. Thus, three images (prescan, baseline-scan, and drug-scan) are acquired.

Figure 7:
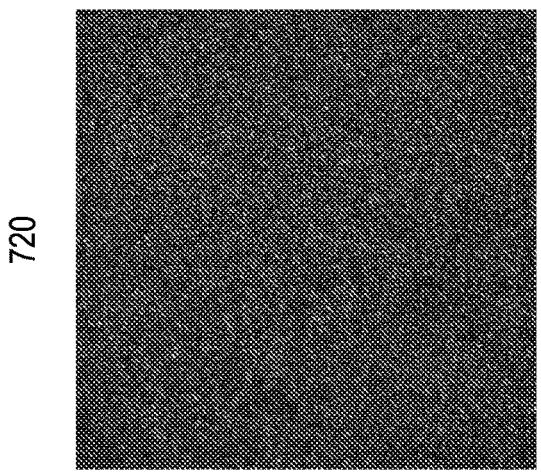
FIG. 7 is a series of images illustrating a fluorescent image of a bottom bead, a phase contrast image, and a fluorescent image of a yellow/green bead.
Figure 7:
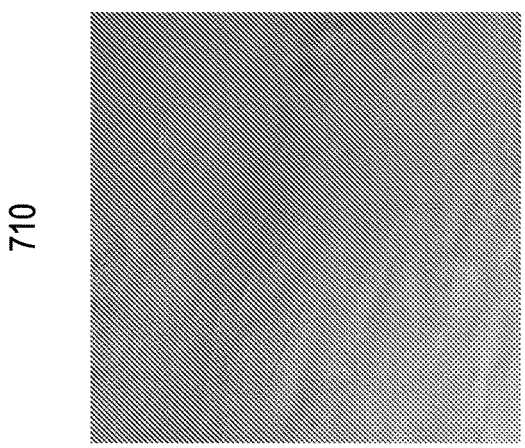
Figure 7:
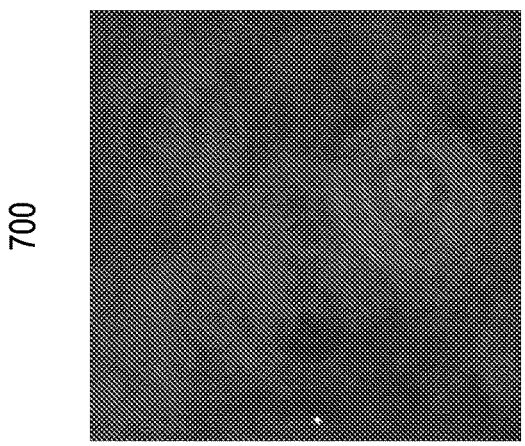
Figure 10:
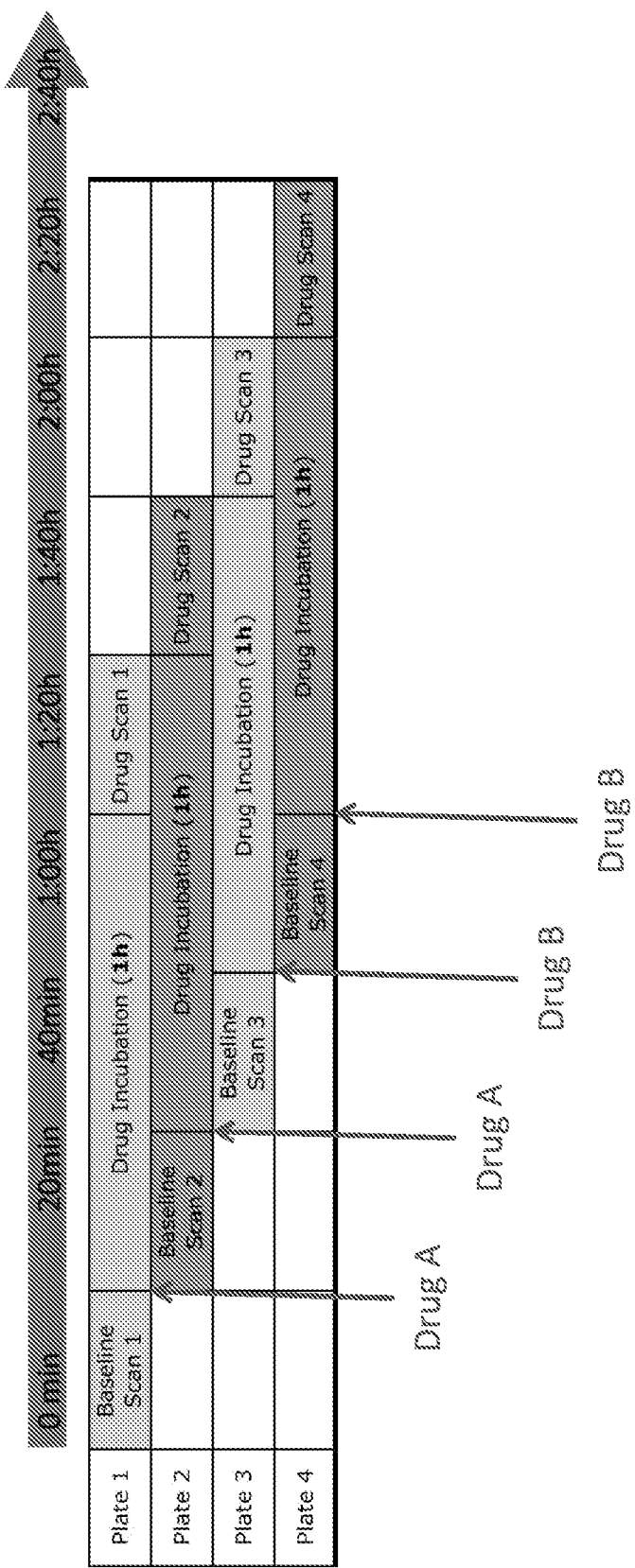
FIG. 10 illustrates an example process flow diagram 1000 for high-throughput screening using cellular contraction.

FIG. 7 is a series of images illustrating a set of three example acquired images. At 700 is a fluorescent image of a bottom bead (0.5 μm). At 710 is a phase contrast image. At 720 is a fluorescent image of a yellow/green bead 0.2 μm. Root mean square values of the absolute traction forces were calculated before and after adding drugs. FIG. 10 illustrates an example process flow diagram 1000 for high-throughput screening using cellular contraction. For example, using the process illustrated in FIG. 10 and a 96 well plate, each scan takes approximately 15 minutes. Since each plate goes through a baseline scan, drug incubation (60 minutes), and a drug scan, it takes approximately 90 minutes per plate.

Figure 8:
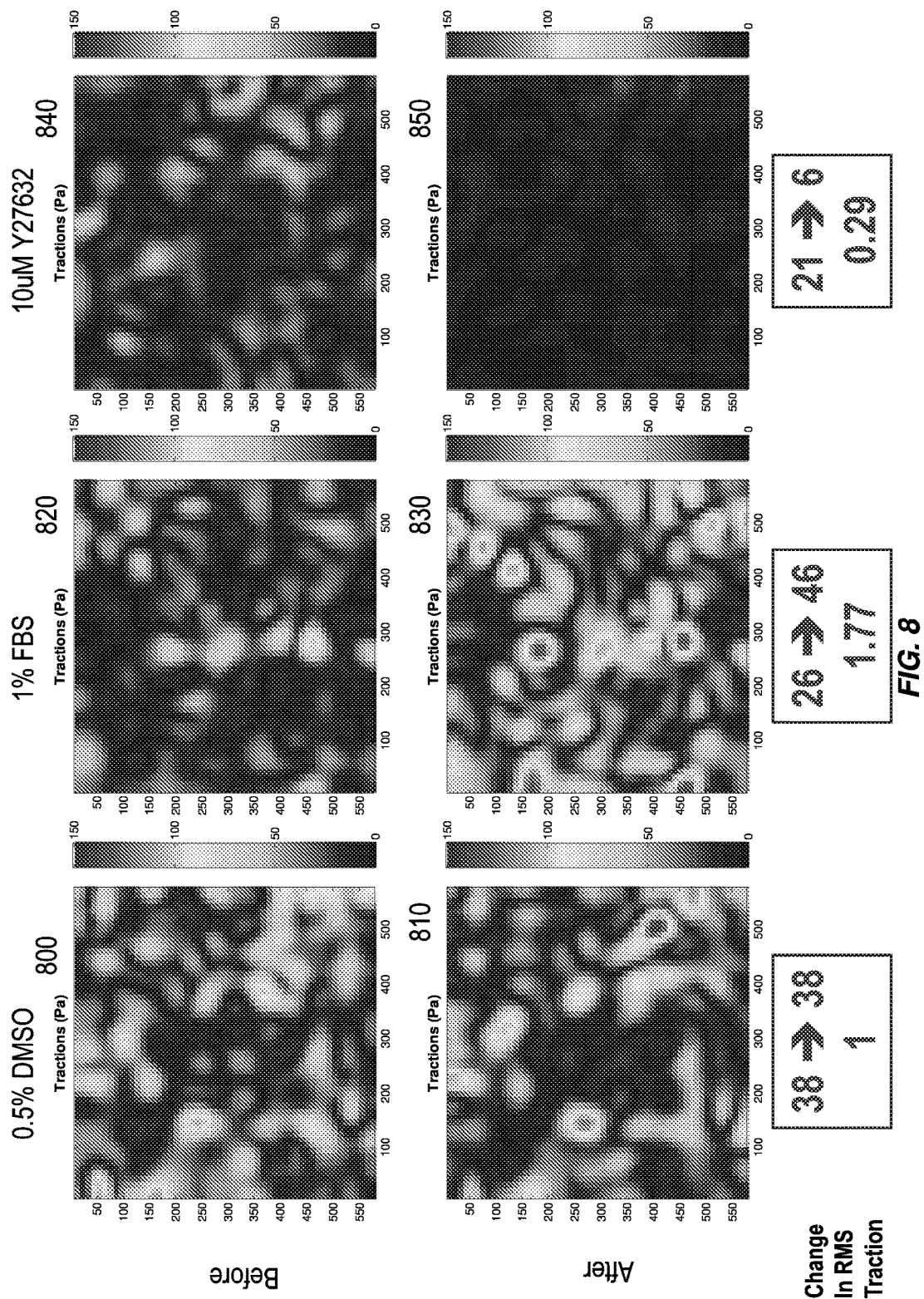
FIG. 8 is a series of images illustrating six absolute cell traction maps.

Drug-induced changes in traction provide a simple and physiologically relevant index to identify hits, i.e., those molecules that appreciably reduce cellular traction forces. FIG. 8 is a series of images illustrating six absolute cell traction maps. At 800-850 are cell traction maps for 0.5% Dimethylsulfoxide (DMSO), 1% Fetal Bovine Serum (FBS), 10 μM Y27632, both before and after adding drugs. Y27632 is an inhibitor of the Rho-associated protein kinase, which is known to reduce cellular contraction. As can be seen in FIG. 8, the measured change in RMS traction was 1, 1.77, and 0.29 respectively. Specifically, the treatment with 0.5% DMSO did not change the RMS (root mean square) traction. The treatment of 1% FBS increased RMS traction by 77% from the baseline. The treatment of 10 uM Y-27632 decreased RMS traction by 71% from the baseline. The ratio of RMS tractions of before and after drug treatment (or, normalized contraction) is an index to evaluate the effects of drugs in both stiffening and softening responses.

Figure 11:
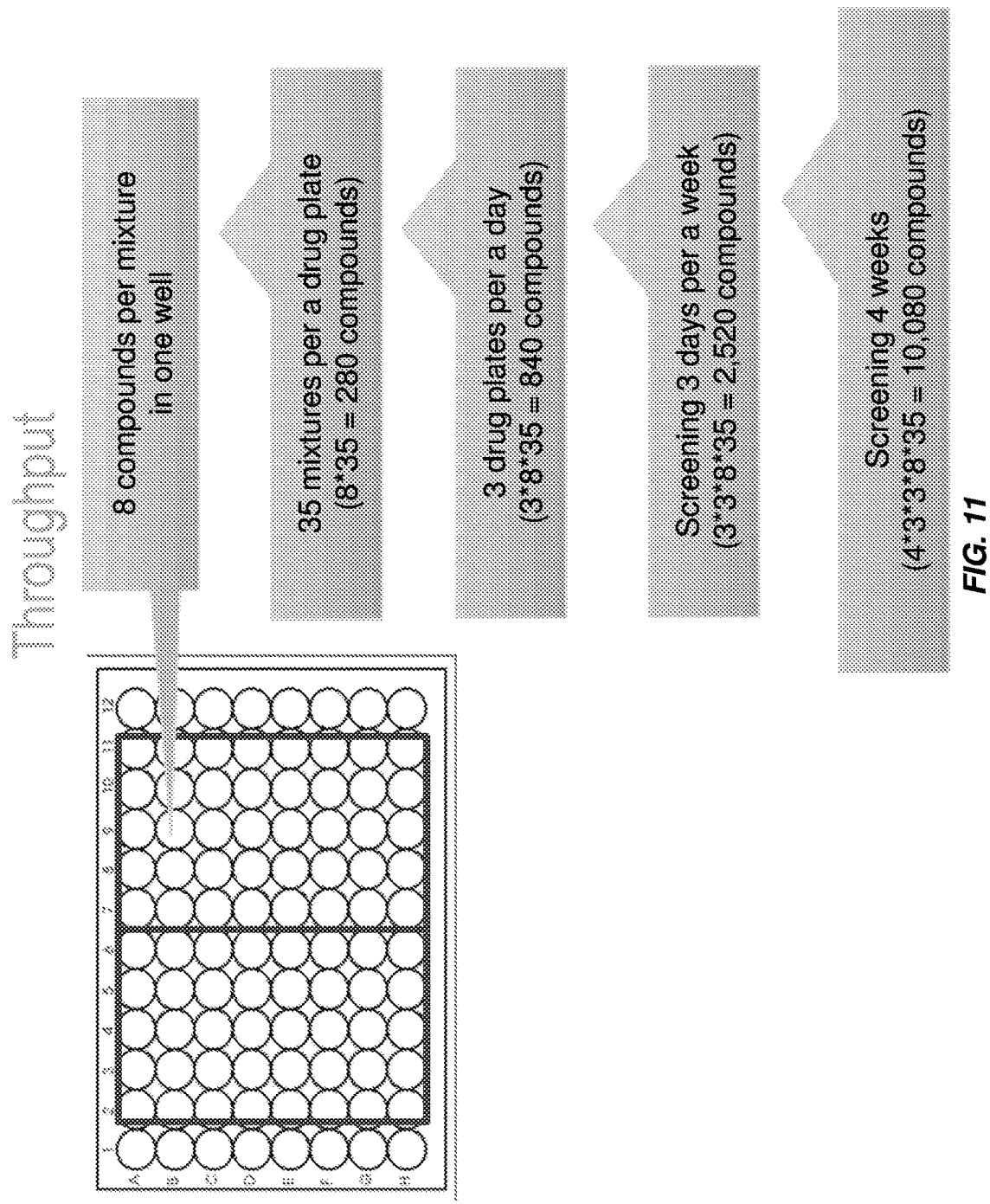
Figure 12:
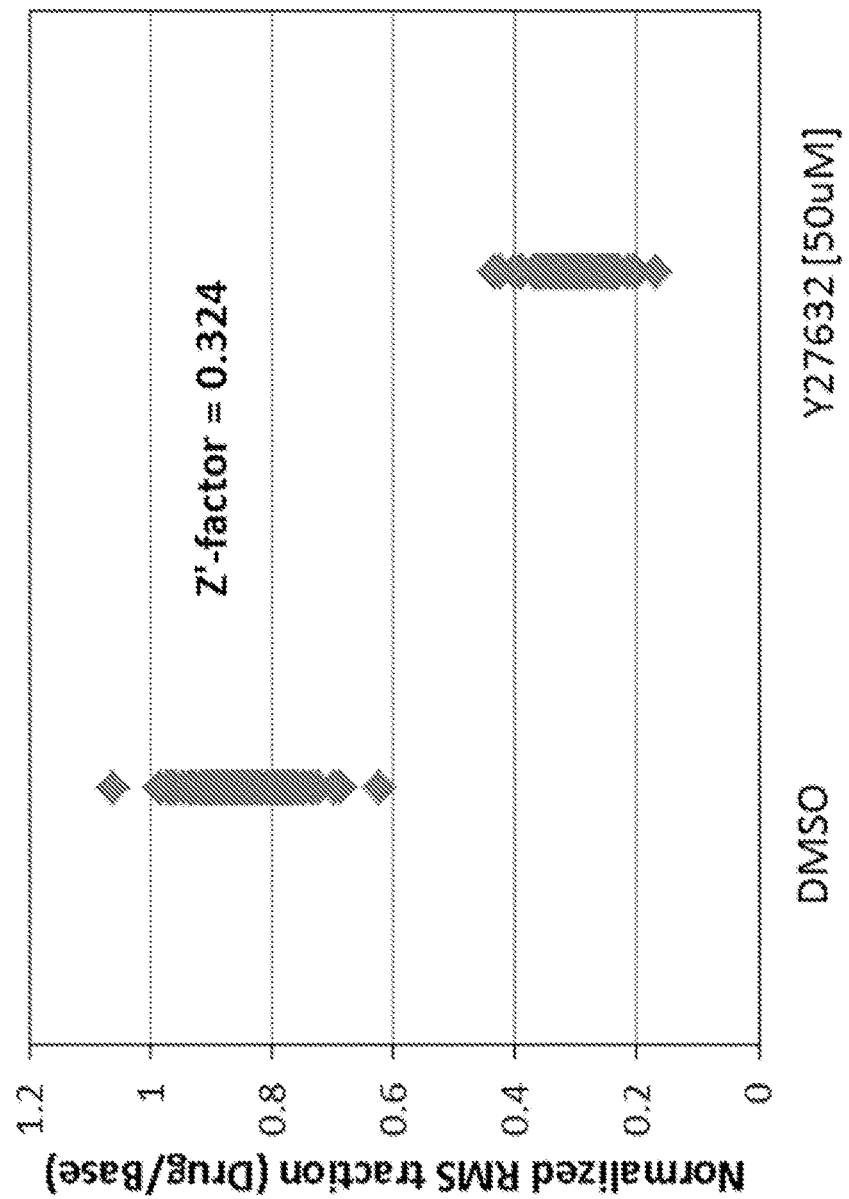

Using HTTM, a library of 10,000 small molecular compounds that have drug-like properties was screened. As shown in FIG. 11, by simultaneously screening mixtures of eight compounds, two thousand compounds per week were evaluated in quadruplicate. After retesting individual compounds from initially positive wells, eight individual compounds were identified that relaxed HASM cells. FIG. 12 is a plot illustrating the measured Z'-factor or normalized traction for DMSO and iso(50 μM). As evident in FIG. 12, DMSO exhibited a normalized traction above 0.5, whereas iso(50 μM) exhibited a normalized traction below 0.5. The Z-factor is defined in terms of four parameters: the means and standard deviations of both the positive (p) and negative (n) controls ($\mu_p$, $\sigma_p$, $\mu_n$, and $\sigma_n$). Given these values, the Z-factor is defined as:

$$Z\text{-factor} = 1 - \frac{3(\sigma_p + \sigma_n)}{|\mu_p - \mu_n|}.$$

Figure 13:
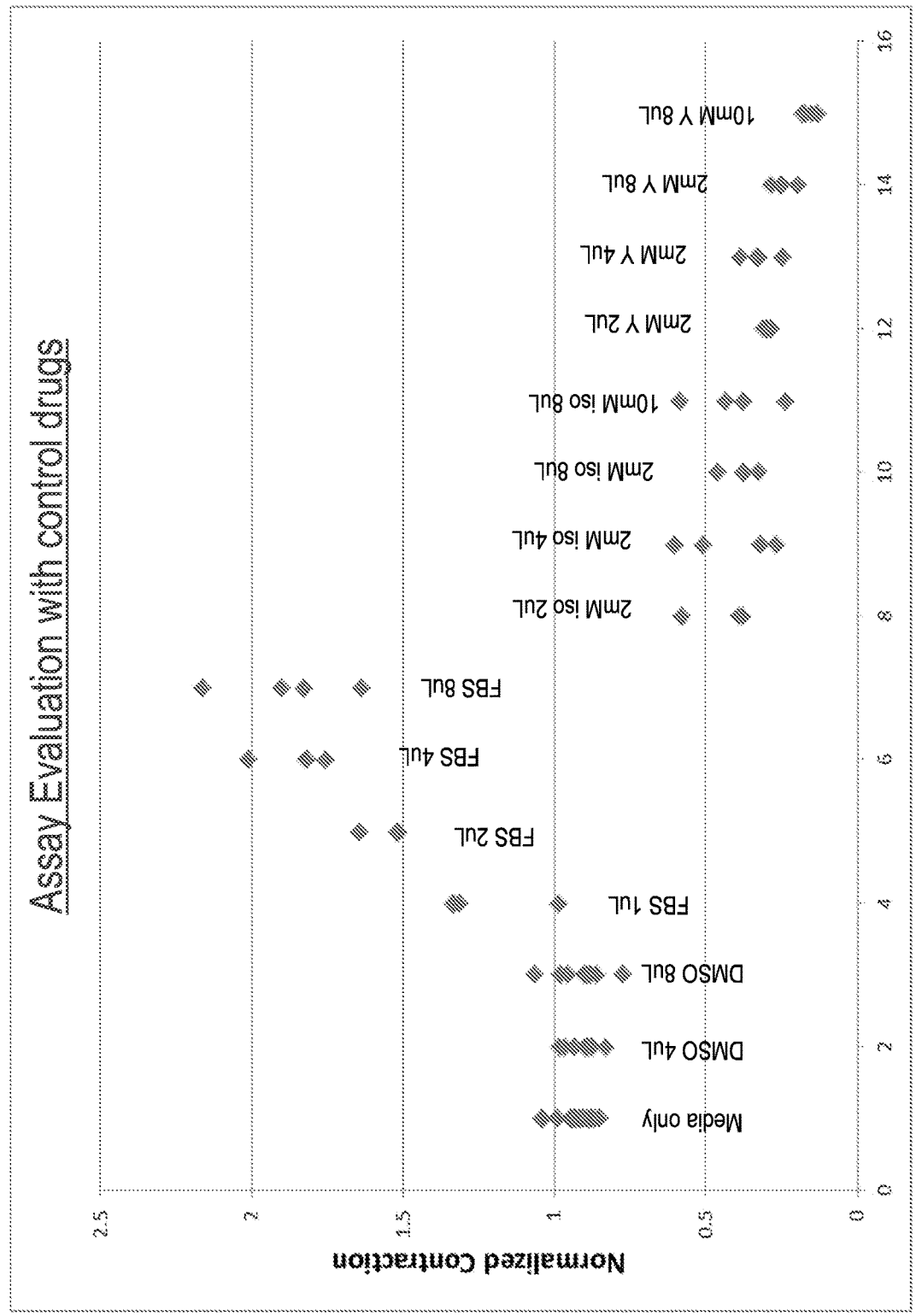
FIG. 13 is a plot of assay evolution with drug control illustrating a normalized contraction for each of the specified control drugs.

FIG. 13 is a plot of assay evolution with drug control illustrating a normalized contraction for each of the specified control drugs. To evaluate the assay, known drugs were tested in doses shown in FIG. 13. Media alone as well as 4 μL, and 8 μL of DMSO showed little change in cellular contraction (presented as RMS traction). Additionally, 4 uL of DMSO was added as a negative control for the assay. Increasing doses of FBS (2 μL, 4 μL, and 8 μL) showed increased the cellular traction in a dose dependent manner. To ensure large contraction, 8 uL of FBS was utilized as one of positive control drugs. Increasing doses of isoproterenol (iso) showed decreasing cellular contraction (more than 50%) but the response did not appear dose dependent. 4 uL of 10 mM iso was used as a positive controls. Increasing doses of Y-27632 showed decreasing cellular contraction in a dose dependent manner. 4 uL of 10 mM Y-27632 was used as a positive control. Thus, 4 uL of DMSO was used as a negative control, 8 uL of FBS (100%), 4 uL of iso(10 mM in DMSO), and 4 uL of Y-27632 (10 mM in DMSO) were used as 3 positive controls that were added to compounds for screening. Since the example screen was for drugs that reduce contraction of human airway smooth muscle cells, drugs that reduce contraction are labeled as positive hits, drugs that increase contraction are labeled "negative hits."

Figure 14:
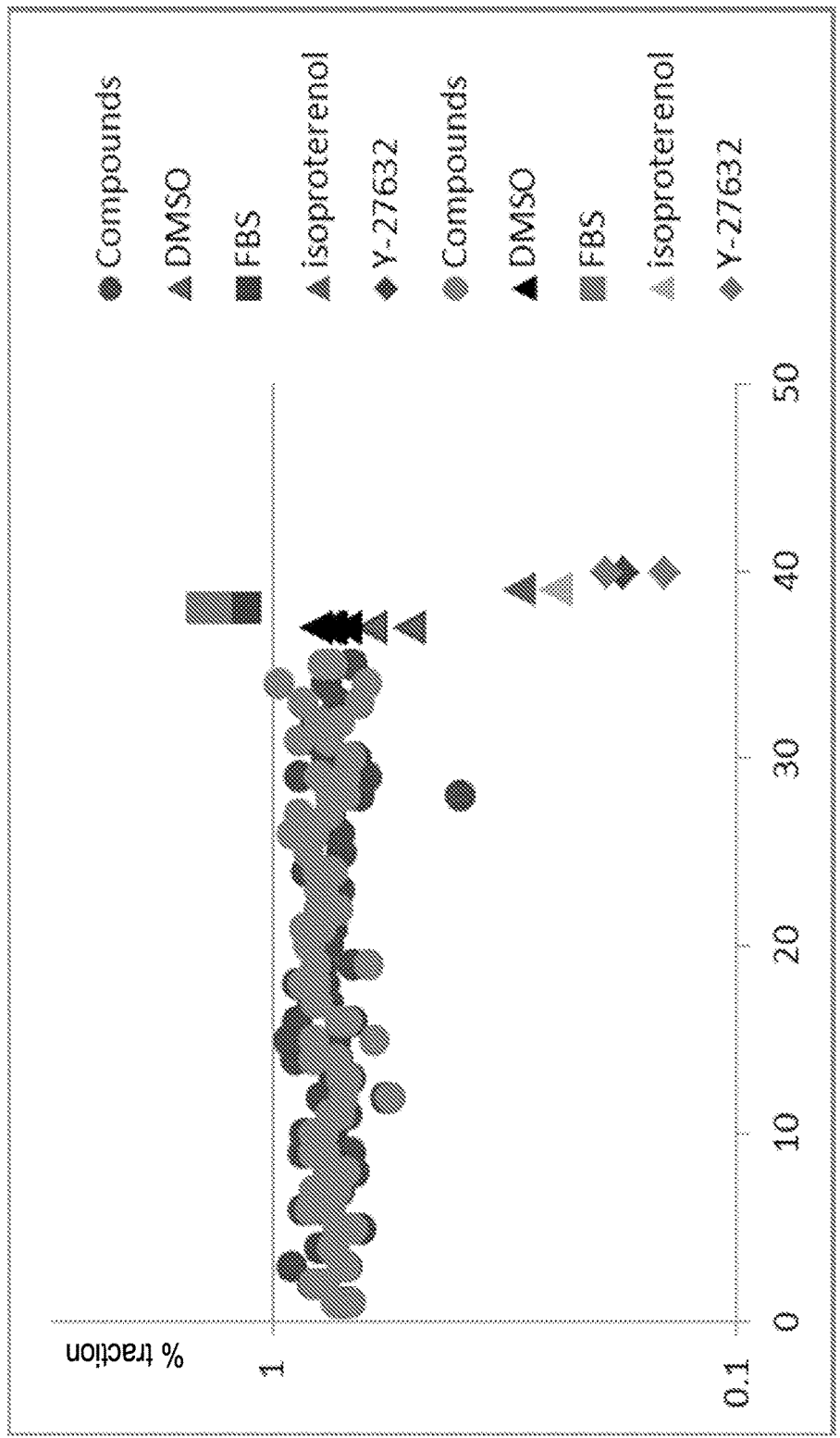
FIG. 14 is a plot illustrating the percent traction of a number of drugs on a "zero-hit" drug plate.

FIG. 14 is a plot illustrating the percent traction of a number of drugs on a "zero-hit" drug plate. The number of drug IDs is shown along the X-axis. Control drug IDs are 37(DMSO), 38(FBS), 39(iso) and 40(Y-27632). The normalized traction (RMS traction after adding drug/RMS traction before adding drug) is shown on the Y-axis. Circles illustrate mixtures of compounds (ID: 1~35). Consistently, DMSO did not significantly alter traction, FBS increased traction, iso & Y-27632 decreased traction. In the drug plate shown in FIG. 14, however, DMSO decreased cellular contraction by the greatest percentage.

Figure 15:
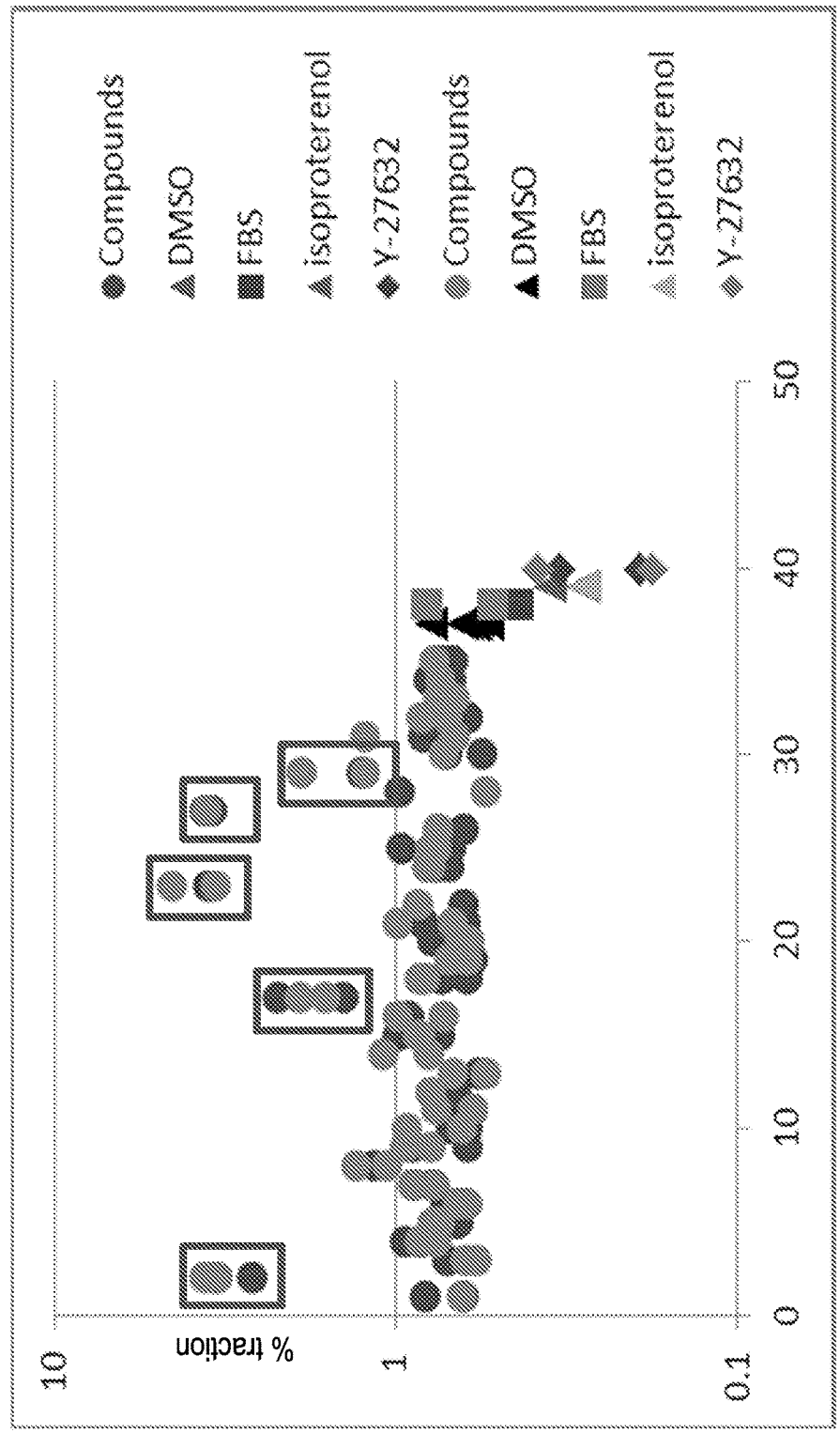
FIG. 15 is a plot illustrating the percent traction of a number of drugs on a "negative-hit" drug plate.

FIG. 15 is a plot illustrating the percent traction of a number of drugs on a "negative-hit" drug plate. A negative hit is a result that shows increased contraction. The drug plate shown in FIG. 15 illustrates five mixtures that induce an increase of contraction.

Figure 16:
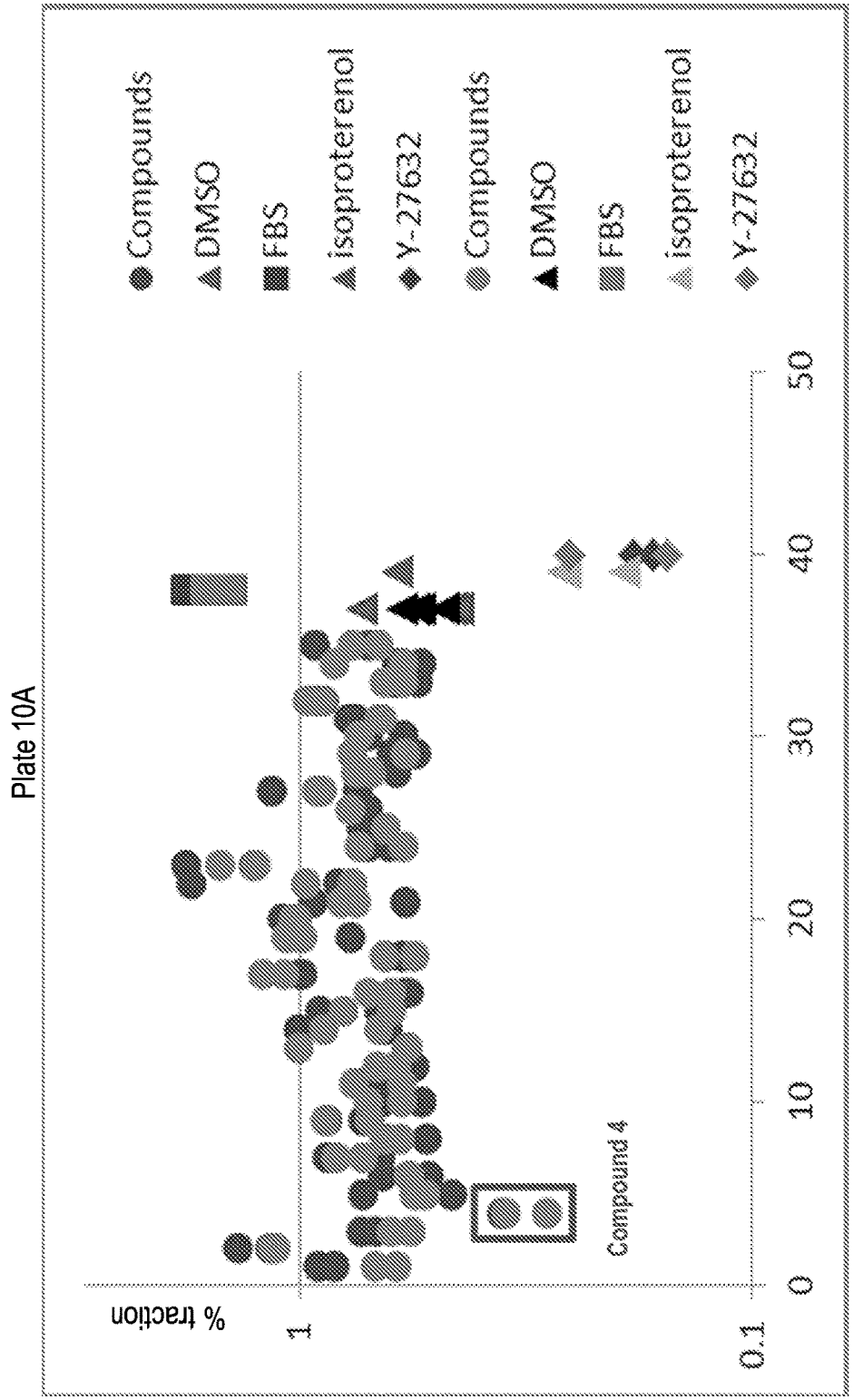
FIG. 16 is a pot illustrating the percent traction of a number of drugs on a "positive-hit" drug plate.

FIG. 16 is a plot illustrating the percent traction of a number of drugs on a "positive-hit" drug plate. Mixture number four shows a positive hit.

Figure 17:
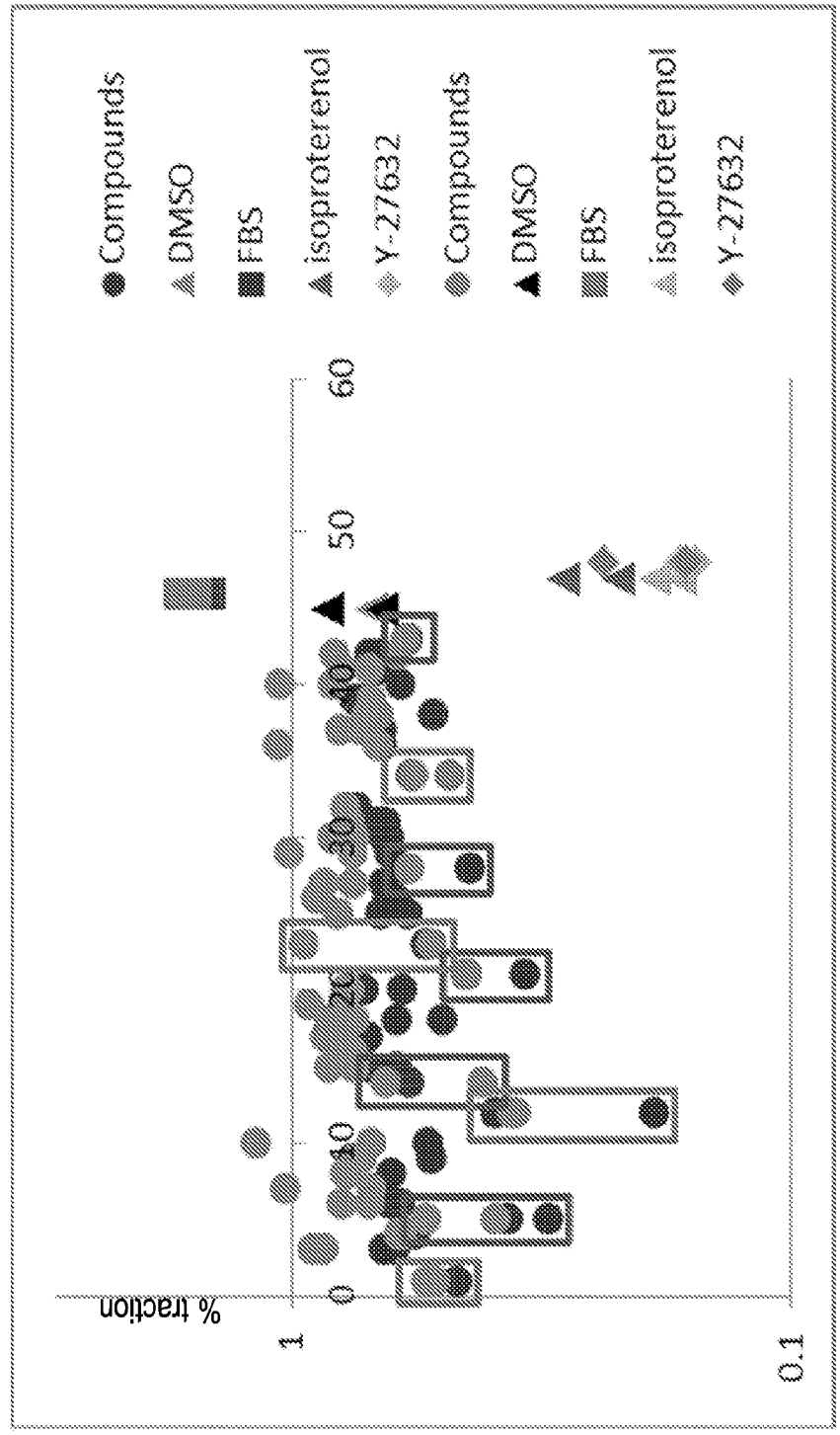
FIG. 17 is a plot illustrating the percent traction of a number of drugs on a de-convoluted drug plate.

FIG. 17 is a plot illustrating the percent traction of a number of drugs on a de-convoluted drug plate. Green boxes indicate the replication of the mixtures that were found to reduce contraction and the red boxes indicate single compounds that showed the effects.

As illustrated in example 3, HTTM provides a convenient, rapid, and inexpensive platform for drug discovery based upon a physiological endpoint, namely, cell contractile force.

Other Embodiments

Other embodiments are within the scope and spirit of the appended claims. Having thus described at least one aspect of the invention, various alternations, modifications and improvements will readily occur to those skilled in the art. Such alternations, modifications and improvements are intended to be within the scope and spirit of the invention. Accordingly, the foregoing description is by way of example only and is not intended as limiting.

What is claimed is:

1. A platform for biological assays, comprising:
a base substrate providing structural support to the platform, at least one surface of the base substrate coated with position markers and a deformable layer positioned on top of the base substrate, wherein said deformable layer comprises a plurality of detectable deformation markers embedded throughout or adherent to an exposed surface of said deformable layer; and
a top plate positioned on top of the deformable layer, the top plate having multiple through holes and plasma-clean bonded to the deformable layer such that the through holes form well walls and portions of a surface of the deformable layer forms well bottoms, wherein the top plate is water impermeable and the first deformable layer is water impermeable to prevent cross contamination between wells.

2. The platform of claim 1, wherein said deformation markers comprises fluorescent beads.

3. A platform for biological assays, comprising:
a base substrate providing structural support to the platform,
a first deformable layer positioned on top of the base substrate; and
a top plate positioned on top of the first deformable layer, said top plate comprising multiple through holes,
wherein said first deformable layer is plasma-clean bonded to said top plate such that the through holes form well walls and portions of a surface of the deformable layer forms well bottoms, wherein the top plate is water impermeable and the first deformable layer is water impermeable to prevent cross contamination between wells, and wherein the Young's modulus of said first deformable layer and said top plate are different.

4. The platform of 3, wherein said deformable layer comprises a Young's modulus of 0.1 kPa to 1 megapascal (MPa).

5. The platform of 3, wherein said deformable layer comprises a Young's modulus of 1-75 kPa.

6. The platform of 3, wherein said deformable layer comprises a Young's modulus of 100 pascal (Pa) to 1 kPa.

7. The platform of claim 3, wherein said deformable layer comprises a Young's modulus of less than 10 kPa.

8. The platform of claim 3, wherein said deformable layer comprises a Young's modulus of 8 to 17 kPa.

9. The platform of claim 3, wherein said deformable layer comprises a Young's modulus of 25 to 40 kPa.

10. The platform of claim 3, wherein said top plate comprises 2-2000 well-forming through holes.

11. The platform of claim 10, wherein said through holes in the top plate are arranged in a microtiter plate format, and includes 6, 24, 96, 384 or 1536 well-forming through holes.

12. The platform of claim 3, wherein said deformable layer comprises a thickness of 50-300 μm.

13. The platform of claim 3, wherein said deformable layer or said top plate comprises a silicone polymer.

14. The platform of claim 13, wherein said polymer comprises a silicon elastomer.

15. The platform of claim 14, wherein elastomer comprises polydimethylsiloxane (PDMS).

* * * * *